(12) United States Patent
Miyagi et al.

(10) Patent No.: US 10,085,712 B2
(45) Date of Patent: Oct. 2, 2018

(54) APPARATUS CAPABLE OF CONNECTING CONNECTOR OF ULTRASONIC PROBE

(71) Applicant: TOSHIBA MEDICAL SYSTEMS CORPORATION, Otawara-shi (JP)

(72) Inventors: Takeshi Miyagi, Fujisawa (JP); Tomohiro Sato, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 668 days.

(21) Appl. No.: 14/676,040

(22) Filed: Apr. 1, 2015

(65) Prior Publication Data

US 2015/0320389 A1  Nov. 12, 2015

(30) Foreign Application Priority Data

May 9, 2014 (JP) ................................ 2014-097627

(51) Int. Cl.
*A61B 8/00* (2006.01)
(52) U.S. Cl.
CPC .................. *A61B 8/00* (2013.01); *A61B 8/44* (2013.01); *A61B 8/4405* (2013.01); *A61B 8/4427* (2013.01); *A61B 8/4433* (2013.01); *A61B 8/4444* (2013.01); *A61B 8/546* (2013.01); *A61B 8/4411* (2013.01)

(58) Field of Classification Search
CPC ........... A61B 8/00; A61B 8/4427; A61B 8/44; A61B 8/4444; A61B 8/546; A61B 8/4433; A61B 8/4405; A61B 8/4411
See application file for complete search history.

(56) References Cited

U.S. PATENT DOCUMENTS 5,560,362 A * 10/1996 Sliwa, Jr. ............... A61B 8/546
600/439

FOREIGN PATENT DOCUMENTS

| JP | 63-087895 U | 6/1988 |
|---|---|---|
| JP | 2007-244583 A | 9/2007 |
| JP | 2008-142221 A | 6/2008 |

* cited by examiner

*Primary Examiner* — Joel Lamprecht
(74) *Attorney, Agent, or Firm* — Oblon, McClelland, Maier & Neustadt, L.L.P.

(57) ABSTRACT

An apparatus capable of connecting a connector of ultrasonic probe includes a connected part, a wall part and a vent hole. The connected part is provided in a housing and is configured to be capable of connecting a connector of ultrasonic probe. The wall part is provided in a location to surround side faces of the connector in a state of being connected to the connected part. The vent hole is provided between the connected part and the wall part so as to pass through from outside to inside of the housing.

20 Claims, 24 Drawing Sheets

APPARATUS CAPABLE OF CONNECTING CONNECTOR OF ULTRASONIC PROBE

CROSS-REFERENCE TO RELATED APPLICATION

This application is based upon and claims the benefit of priority from Japanese Patent Application No. 2014-97627, filed on May 9, 2014, the entire contents of which are incorporated herein by reference.

FIELD

One embodiment of the present invention relates to an apparatus capable of connecting a connector of ultrasonic probe.

BACKGROUND

In the field of medical applications, ultrasonic diagnostic apparatuses have been used which utilize ultrasonic waves generated by using multiple transducers (piezoelectric transducers) of ultrasonic probe to image the interior of an object. An ultrasonic diagnostic apparatus transmits ultrasonic waves into are object from an ultrasonic probe connected to the ultrasonic diagnostic apparatus, and receives reflected waves, which are caused by inconsistencies of acoustic impedance in the interior of the object, with an ultrasonic probe. The ultrasonic diagnostic apparatus generates reception signals based on reflected waves received by the ultrasonic probe and obtains a desired ultrasonic image by image processing.

Here, each transducer of the ultrasonic probe is typically formed of a piezoelectric ceramic (for example, lead zirconate titanate (PZT)). Each transducer generates undesired ultrasonic waves in a direction opposite to the direction of the object, and such undesired sonic waves are absorbed by a sound absorption material typically called as a backing to be transformed into heat and discharged.

On the other hand, ultrasonic probes of recent years have made it possible to see a three-dimensional stereo image in real time by disposing transmitting/receiving elements of ultrasonic wave in a two-dimensional array. However, disposing transmitting/receiving elements in a two-dimensional array results in increase in the number of signals and for the processing thereof, integrated circuits of a larger scale become required. As a result of this, heat generation increases in the integrated circuits incorporated in an ultrasonic probe, particularly inside a probe connector, thus causing a problem of increase in the surface temperature of the probe connector in which particularly a large number of integrated circuits are incorporated.

To cope with this problem, there is disclosed an ultrasonic probe which has a structure for transferring heat generated in semiconductors in a probe connector to a duct in the probe connector by using a heat pipe etc. This structure allows cooling of the probe connector by air flowing in the duct.

There is also disclosed an ultrasonic probe having a structure in which a heat sink is provided at a portion where a probe connector is connected with the ultrasonic diagnostic apparatus. This structure allows the probe connector to be cooled by a heat sink being inserted into a duct inside the ultrasonic diagnostic apparatus.

However, conventional structures have problems in reliability and ease of use, etc. To be specific, in one of the conventional structures, since an inlet port for air must be opened in a housing (case) of the probe connector, there is possibility that liquids such as chemicals come into the probe connector during use of the ultrasonic probe and sterilization thereof, thereby causing malfunctions.

The other of the conventional structures has a problem that the structure of the probe connector becomes complicated and the weight of the entire ultrasonic probe increases, so that handling thereof becomes difficult, and in addition to that, the probe connector is likely to be broken during attachment/detachment of the probe connector to/from an ultrasonic diagnostic apparatus when the ultrasonic probe is replaced with one compatible with the purpose of testing.

BRIEF DESCRIPTION OF THE DRAWINGS

In accompanying drawings.

DETAILED DESCRIPTION

An apparatus capable of connecting a connector of ultrasonic probe relating to the present embodiment will be described with reference to appended drawings.

To solve the above-described problems, the present embodiment provides the apparatus capable of connecting a connector of ultrasonic probe, including: a connected part provided in a housing and configured to be capable of connecting a connector of ultrasonic probe; a wall part provided in a location to surround side faces of the connector in a state of being connected to the connected part; and a vent hole provided between the connected part and the wall part so as to pass through from outside to inside of the housing.

To solve the above-described problems, the present embodiment provides the apparatus capable of connecting a connector of ultrasonic probe, including: a connected part provided in a housing and configured to be capable of connecting a connector of ultrasonic probe; a wall part provided in a location to surround side faces of the connector in a state of being connected to the connected part; and a vent hole provided in the wall part so as to pass through from outside to inside of the housing.

(First Embodiment)

Using FIGS. 1 to 8, an apparatus capable of connecting a connector of ultrasonic probe relating to a first embodiment will be described. Description will be made taking an example in which the apparatus capable of connecting a connector of ultrasonic probe relating to the first embodiment is an ultrasonic diagnostic apparatus.

Figure 1:
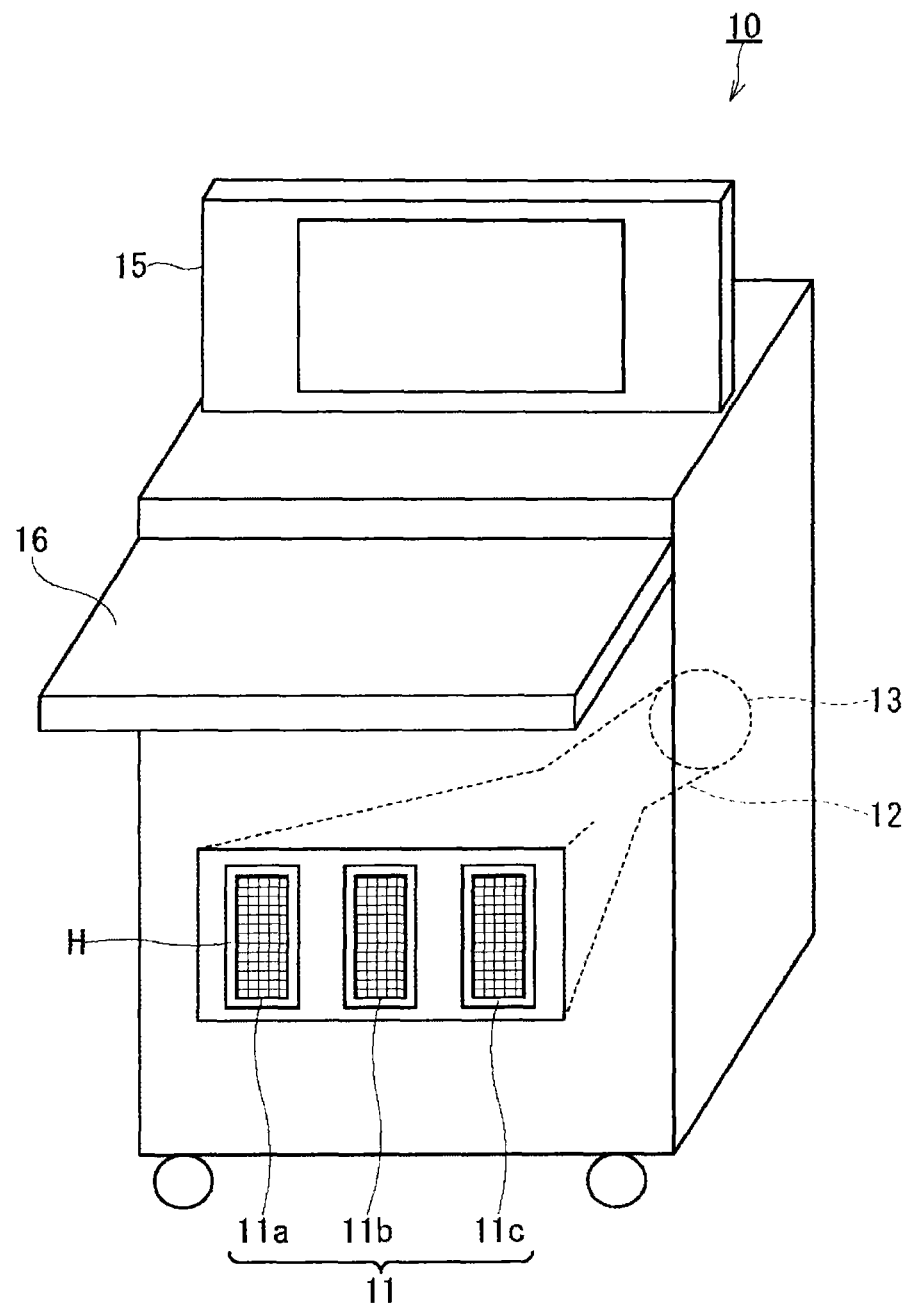
FIG. 1 is a perspective view illustrating an appearance of an ultrasonic diagnostic apparatus relating to a first embodiment.
Figure 2:
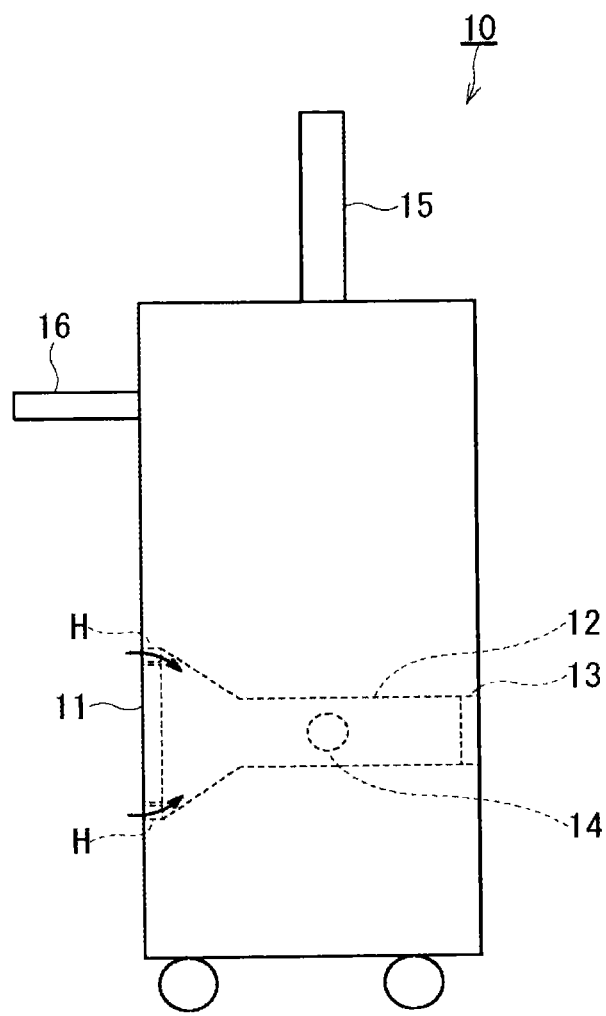
FIG. 2 is a diagram illustrating an appearance of a side face of the ultrasonic diagnostic apparatus relating to the first embodiment.

1-1. Description of Structure of Ultrasonic Diagnostic Apparatus Relating to First Embodiment FIG. 1 is a perspective view illustrating an appearance of an ultrasonic diagnostic apparatus relating to a first embodiment. FIG. 2 is a diagram illustrating an appearance of a side face of the ultrasonic diagnostic apparatus relating to the first embodiment.

FIGS. 1 and 2 illustrate an ultrasonic diagnostic apparatus 10 relating to the first embodiment. The ultrasonic diagnostic apparatus 10 contains, in its interior, substrates with integrated circuits mounted thereon, storage devices, and so on. The ultrasonic diagnostic apparatus 10 includes an apparatus connector unit 11, a duct tube (air duct and tube, etc.) 12, a blower (fan etc.) 13, an air velocity sensor 14, a display device 15, and an input device 16. Note that the air velocity sensor 14 is not an indispensable component.

The apparatus connector unit 11 is provided in a side face, for example, in a front face of the housing of the ultrasonic diagnostic apparatus 10. The apparatus connector unit 11 includes three apparatus connectors (connected parts) 11a, 11b, and 11c to which a probe connector C (illustrated in FIG. 5) of an ultrasonic probe P (illustrated in FIG. 5) is connectable. Note that the number of apparatus connectors may be one or more, without being limited to 3. Moreover, the arrangement of the plurality of apparatus connectors will not be limited to a lateral arrangement, and may be a longitudinal, or a lateral and longitudinal arrangement.

Figure 3:
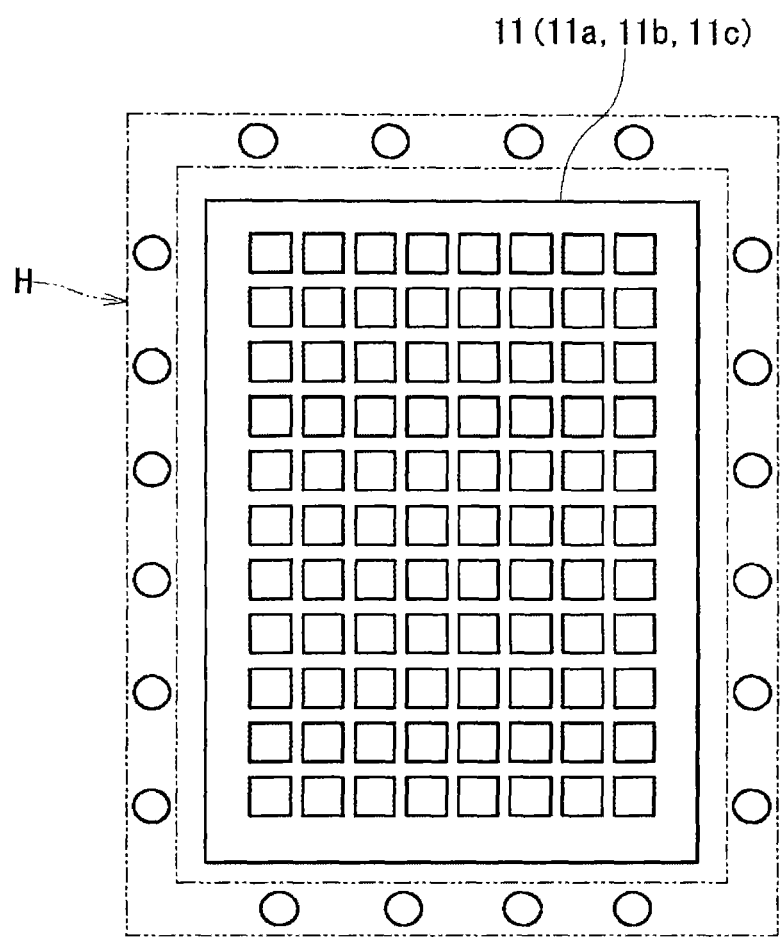
FIG. 3 is a partially enlarged view illustrating a first structural example of an apparatus connector and a vent hole.
Figure 4:
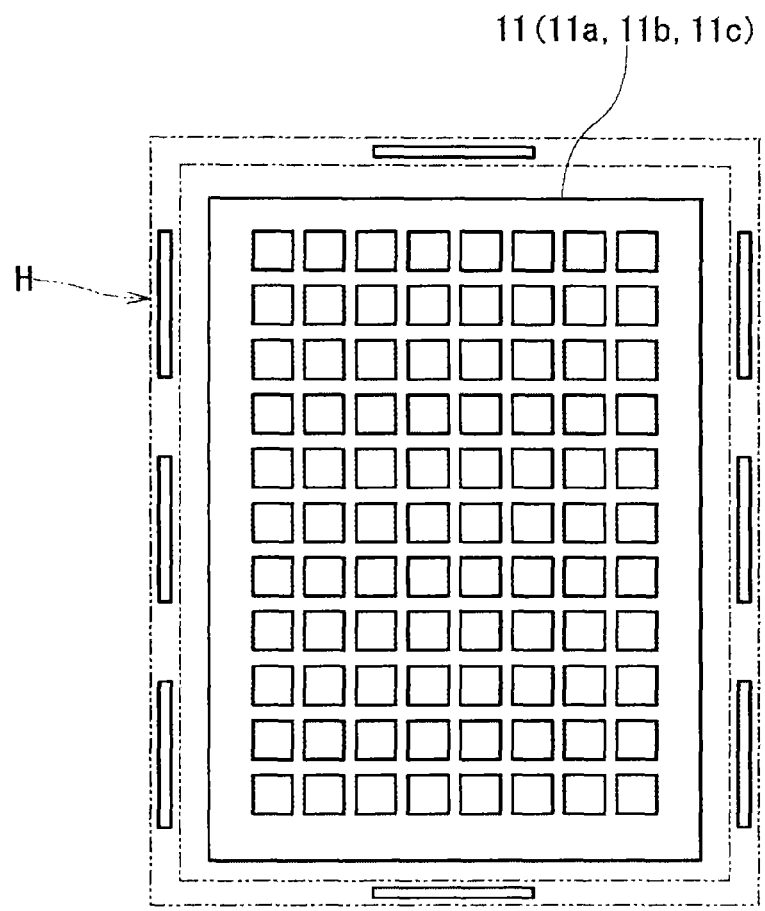
FIG. 4 is a partially enlarged view illustrating a second structural example of an apparatus connector and a vent hole.

FIG. 3 is a partially enlarged view illustrating a first structural example of an apparatus connector and a vent hole. FIG. 4 is a partially enlarged view illustrating a second structural example of an apparatus connector and a vent hole.

As illustrated in FIGS. 3 and 4, the apparatus connector 11a (as with the apparatus connectors 11b and 11c) of the apparatus connector unit 11 is a connected part to which a connection part (pin) of the probe connector C (illustrated in FIGS. 6 and 7) is connectable, and electric connection with the probe connector C is established via the apparatus connector 11a. Moreover, one or more vent holes H are formed in a circumferential portion of the apparatus connector 11a (as with the apparatus connectors 11b and 11c), that is, in the outside of the apparatus connector 11a. The vent hole H will have an equivalent effect whether it has a circular shape as illustrated in FIG. 3 or a slit shape as illustrated in FIG. 4.

Note that the vent hole H may include at least one of a dust filter for shielding dust in the air drawn to the inside through the vent hole H, and an electromagnetic shield (metal mesh) for shielding electromagnetic waves radiated by the probe connector C.

Referring back to the description of FIGS. 1 and 2, the duct tube 12 is provided within the ultrasonic diagnostic apparatus 10. The duct tube 12 is a guide part which forms an air path between the vent hole H in the front face of the ultrasonic diagnostic apparatus 10 and the rear face of the ultrasonic diagnostic apparatus 10, and thereby guides the air inside the housing of the ultrasonic diagnostic apparatus to the outside, or the air outside the housing of the ultrasonic diagnostic apparatus 10 to the inside, through the vent hole H.

The blower 13 is provided in the air path formed by the duct tube 12, for example, in the rear face of the ultrasonic diagnostic apparatus 10 and at an end part of the air path, and generates a flow of air in the duct tube 12. The blower 13 has a capability of drawing in the air outside the front face of the ultrasonic diagnostic apparatus 10 to the inside from the vent holes H (as illustrated by arrows in FIG. 2), guiding the air drawn to the inside to the rear face of the ultrasonic diagnostic apparatus 10 via the duct tube 12, and blowing out the air guided to the rear face to outside the rear face of the ultrasonic diagnostic apparatus 10. Alternatively, the blower 13 also has a capability of drawing in the air outside the rear face of the ultrasonic diagnostic apparatus 10, guiding the air drawn to the inside to the front face of the ultrasonic diagnostic apparatus 10 via the duct tube 12, and blowing out the air guided to the front face to outside the front face of the ultrasonic diagnostic apparatus 10 from the vent holes H.

The air velocity sensor 14 is installed in the duct tube 12 and detects the flow velocity of the air flowing in the duct tube 12 due to the action of the blower 13.

Note that FIGS. 1 and 2 illustrate a configuration in which one duct tube 12 and one blower 13 correspond to three apparatus connectors 11a, 11b, and 11c. However, the configuration may be such that one duct tube 12 and one blower 13 correspond to each of the three apparatus connectors 11a, 11b, and 11c.

1-2. Description of Internal Configuration of Ultrasonic Diagnostic Apparatus Relating to First Embodiment FIG. 5 is a schematic view illustrating an internal configuration of the ultrasonic diagnostic apparatus 10 relating to the first embodiment.

Figure 5:
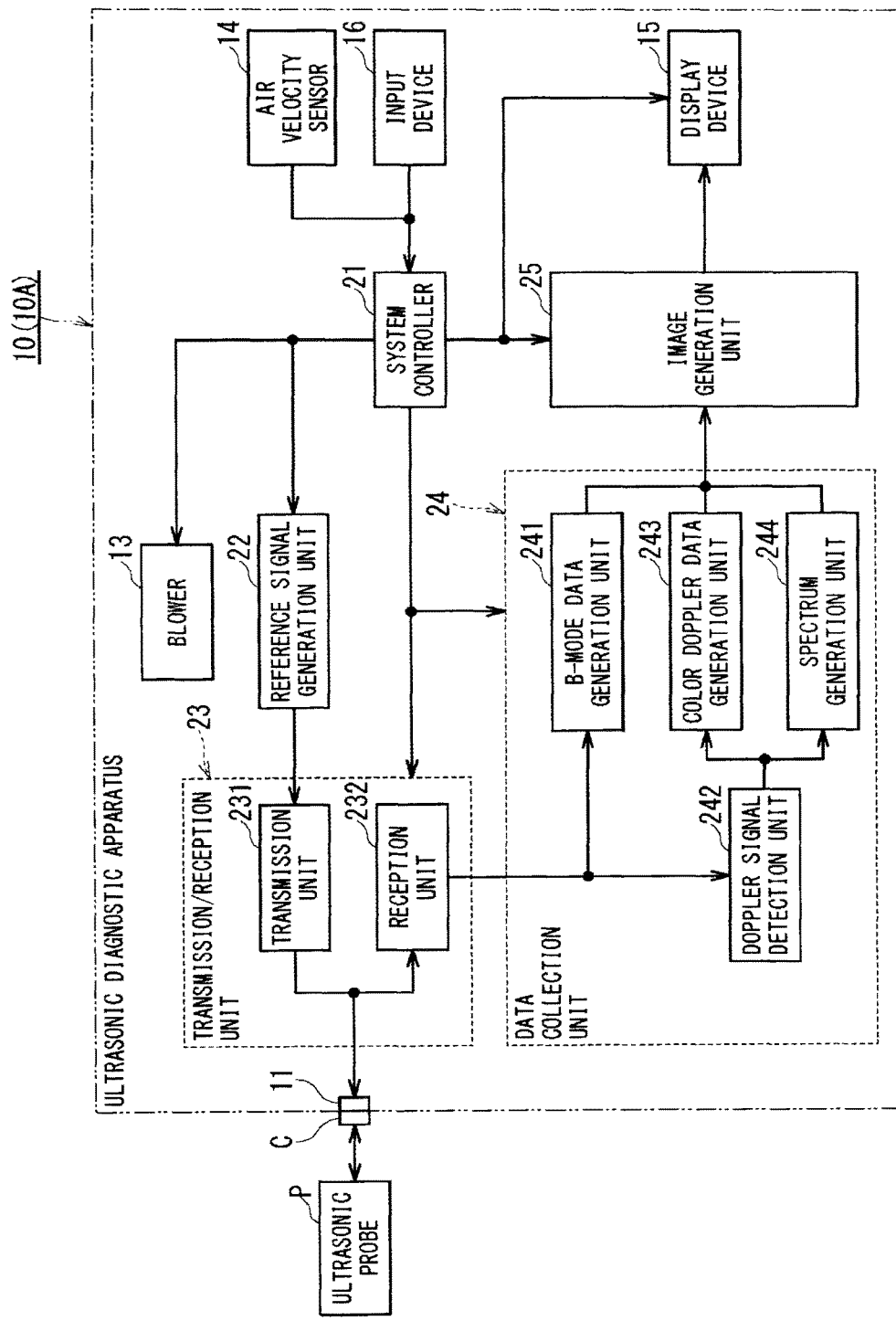
FIG. 5 is a schematic view illustrating an internal configuration of the ultrasonic diagnostic apparatus relating to the first embodiment.

FIG. 5 illustrates an ultrasonic probe P and the ultrasonic diagnostic apparatus 10 relating to the first embodiment. Note that the ultrasonic probe P and the ultrasonic diagnostic apparatus 10 combined may be referred to as an ultrasonic diagnostic apparatus.

The ultrasonic probe P being connected to the ultrasonic diagnostic apparatus 10 transmits and receives ultrasonic waves to and from an object according to control by the ultrasonic diagnostic apparatus 10. The ultrasonic probe P, which is configured to transmit and receive ultrasonic waves with its front face being in contact with the surface of the object, includes a plurality of transducers (piezoelectric transducers) arranged in one or two dimensions at its distal end part. Each transducer, which is an electroacoustic transducer element, has a function of converting electric pulses into ultrasonic pulses (transmitting ultrasonic wave) during transmission, and a function of converting ultrasonic reflected waves (received ultrasonic wave) into electric signals (reception signals) during reception.

The ultrasonic probe P is configured to be compact and light weight and is connected to a transmission unit 231 and a reception unit 232 of a transmission/reception unit 23 (circuit) via a cable (not illustrated). There are different types of ultrasonic probe P, such as a sector-scanning compatible, a linear scanning compatible, and a convex scanning compatible type, and they are arbitrary selected depending on the site of diagnosis. Hereafter, although description will be made on a case where an ultrasonic probe P for sector scanning for the purpose of cardiac function measurement, this case is not limiting, and the ultrasonic probe P may be of a linear scanning compatible or convex scanning compatible type.

The ultrasonic diagnostic apparatus 10 includes an apparatus connector unit 11, a blower 13, an air velocity sensor 14, a display device 15, an input device 16, a system controller 21, a reference signal generation unit 22, a transmission/reception unit 23, a data collection unit 24, and an image generation unit 25.

The blower 13 operates according to control signals from the system controller 21.

The air velocity sensor 14 detects the flow velocity of the air flowing inside the duct tube 12 and transmits it to the system controller 21.

The display device 15 displays image data generated by the image generation unit 25. The display device 15 includes a conversion circuit and a display section (a display), which are not illustrated. The conversion circuit performs D/A conversion and television format conversion on the image data generated by the image generation unit 25 to generate video signals, and displays them on a display.

The input device 16 is made up of various switches, buttons, a trackball, a mouse, and a key board, etc. for taking in various instructions from the operator, conditions, setting instructions of region of interest (ROI), and various image quality conditions setting instructions, and the like into the ultrasonic diagnostic apparatus 10.

The system controller 21 includes a CPU (Central Processing Unit) as a processing circuit and a memory. The system controller 21 integrally controls each unit of the ultrasonic probe P and the ultrasonic diagnostic apparatus 10. Here, if the air inside the duct tube 12 (illustrated in FIGS. 1 and 2) becomes not to flow due to a failure of the blower 13, or the like, the air velocity sensor 14 will detect a flow velocity not more than a threshold value. The system controller 21 may be configured to transmit a signal to stop the action of the ultrasonic probe P in such an occasion.

The reference signal generation unit 22 generates a continuous wave or a rectangular wave, for example, having a frequency substantially equal to the central frequency of an ultrasonic pulse, for the transmission/reception unit 23 and the data collection unit 24 according to a control signal from the system controller 21.

The transmission/reception unit 23 causes the ultrasonic probe P to perform transmission/reception via the apparatus connector unit 11 and the probe connector C according to the control signal from the system controller 21. The transmission/reception unit 23 includes a transmission unit 231 for generating a drive signal for causing the ultrasonic probe P to emit a transmitting ultrasonic wave, and a reception unit 232 for performing phasing addition on a reception signal from the ultrasonic probe P.

The transmission unit 231 includes a rate pulse generator, a transmission delay circuit, and a pulser, which are not illustrated. The rate pulse generator generates a rate pulse for determining a repeating period of transmitting ultrasonic wave by dividing a continuous wave or a rectangular wave supplied from the reference signal generation unit 22, and supplies the rate pulse to the transmission delay circuit. The transmission delay circuit, which is made up of independent delay circuits of a same number (N channels) as that of transducers to be used for transmission, adds a delay time for converging a transmitting ultrasonic wave at a predetermined depth for obtaining a narrow beam width in transmission, and a delay time for emitting a transmitting ultrasonic wave in a predetermine direction, to the rate pulse, and supplies this rate pulse to the pulser. The pulser has independent drive circuits of N channels, and generates drive pulses for driving the transducers incorporated in the ultrasonic probe P based on the rate pulse.

The reception unit 232 of the transmission/reception unit 23 includes a preamplifier, an A/D (Analog-to-Digital) convertor, a reception delay circuit, and an adder, which are not illustrated. The preamplifier, which is made up of N channels, amplifies a minute signal which is converted into an electric reception signal by an transducer to ensure sufficient S/N. The reception signals of N channels which have been amplified to a predetermined quantity at the preamplifier are converted into digital signals by the A/D converter and sent to the reception delay circuit. The reception delay circuit gives a focusing delay time for focusing ultrasonic reflected wave from a predetermined depth, and a deflecting delay time for setting a reception directivity for a predetermined direction to each of the reception signals of N channels outputted from the A/D converter. The adder performs phasing addition on reception signals from the reception delay circuit (reception signals obtained in a predetermined direction are added together with the phases thereof being matched).

The data collection unit 24 collects at least one of B-mode data, color Doppler data, and Doppler spectrum based on reception signals obtained from the transmission/reception unit 23 according to a control signal from the system controller 21. The data collection unit 24 includes a B-mode data generation unit 241, a Doppler signal detection unit 242, a color Doppler data generation unit 243, and a spectrum generation unit 244. The B-mode data generation unit 241 generates B-mode data for reception signals outputted from the adder of the reception unit 232. The B-mode data generation unit 241 includes an envelope wave detector and a logarithmic converter, not illustrated. The envelope wave detector performs envelope detection of reception signals after phasing and adding supplied from the adder of the reception unit 232, and the amplitude of the envelope detection signal is subjected to logarithmic conversion by a logarithmic converter.

The Doppler signal detection unit 242 performs orthogonal detection on the reception signals to detect a Doppler signal. The Doppler signal detection unit 242, which includes a $\pi/2$ phase shifter, a mixer, and an LPF (low pass filter), which are not illustrated, performs orthogonal phase detection on the reception signals supplied from the adder of the reception unit 232, to detect a Doppler signal.

The color Doppler data generation unit 243 generates color Doppler data based on detected Doppler signals. The color Doppler data generation unit 243 includes a Doppler signal storage device, an MTI (moving target indicator) filter, and an autocorrelation calculating element, which are not illustrated. The Doppler signal of the Doppler signal detection unit 242 is temporarily saved in the Doppler signal storage device (not illustrated). The MTI filter, which is a digital filter for high-band passing, reads out a Doppler signal saved in the Doppler signal storage device and performs removal of Doppler components (clutter components), which are caused by respiratory movement and pulsatile movement of organs, on the Doppler signal. The autocorrelation calculating element calculates an autocorrelation value for the Doppler signal in which only blood flow information is extracted by the MTI filter, and further calculates an average flow velocity value and a variance value etc. of blood flow based on the autocorrelation value.

The spectrum generation unit 244 performs FFT analysis on the Doppler signal obtained in the Doppler signal detection unit 242 to generate a frequency spectrum (Doppler spectrum) of the Doppler signal. The spectrum generation unit 244 includes an SH (sample hold) circuit, an LPF (low pass filter), and an FFT (Fast-Fourier-Transform) analyzer, which are not illustrated. Note that each of the SH circuit and LPF is made up of two channels, and each channel is supplied with complex components, that is, a real component (I component) and an imaginary component (Q component), of the Doppler signal outputted from the Doppler signal detection unit 242. The SH circuit is supplied with a Doppler signal outputted from the LPF of the Doppler signal detection unit 242 and a sampling pulse (range gate pulse) which is generated by the system controller 21 dividing a reference signal of the reference signal generation unit 22. In the SH circuit, a Doppler signal from a desired depth is sample-held by a sampling pulse.

Note that this sampling pulse is generated after a delay time from the rate pulse for determining the timing at which a transmitting ultrasonic wave is emitted, and this delay time can be set arbitrarily. The LPF removes stepwise noise components which are superposed on a Doppler signal from a depth, which is outputted from the SH circuit. The FFT analyzer generates a Doppler spectrum based on a smoothed Doppler signal supplied. The FFT analyzer includes a calculating circuit and a storage circuit, which are not illustrated. The Doppler signal outputted from the LPF is temporarily saved in the storage circuit. The calculating circuit performs FFT analysis in a predetermined period of a series of Doppler signals saved in the storage circuit to generate a Doppler spectrum.

According to a control signal from the system controller 21, the image generation unit 25 saves B-mode data and color Doppler data obtained by the data collection unit 24 in correspondence with scanning directions, thereby generating as data a B-mode image and a color Doppler image as the ultrasonic image, and time-sequentially saves a Doppler spectrum and B-mode data obtained with respect to a predetermined scanning direction, thereby generating as data a Doppler spectrum image and an M-mode image as the ultrasonic image.

The image generation unit 25 successively saves B-mode data and color Doppler data for each scanning direction generated by the data collection unit 24, for example, based on a reception signal obtained by ultrasonic transmission/reception for a scanning direction, thereby generating a B-mode image and a color Doppler image. Further, the image generation unit 25 time-sequentially saves B-mode data obtained by multiple times of ultrasonic transmission/reception for a desired scanning direction to generate an M-mode image, and also time-sequentially saves Doppler spectra based on reception signals obtained at a distance in the scanning direction by similar ultrasonic transmission/reception to generate a Doppler spectrum image. That is, a plurality of B-mode images and color Doppler images are saved in an image data storage region of the image generation unit 25, and M-mode images and Doppler spectrum images are saved in a time-sequential data storage region.

Note that the ultrasonic diagnostic apparatus 10 includes a storage device not illustrated. The storage device is a recording medium such as a magnetic disc (a hard disc, etc.), an optical disc (CD-ROM, DVD, etc.), and a semiconductor memory, and an apparatus for reading out information recorded in those media. The storage device stores transmission conditions, predetermined scanning sequences, control programs for performing image generation and displaying, diagnostic information (patient IDs, doctor's opinions, etc.), diagnostic protocols, various signal data and image data, and other groups of data. It is also possible to transfer the data in the storage device to an external apparatus (not illustrated).

1-3. Description of Flow of Air by Ultrasonic Diagnostic Apparatus Relating to First Embodiment FIGS. 6 and 7 are diagrams for explaining the flow of air by the ultrasonic diagnostic apparatus 10 relating to the first embodiment, with the probe connector C being connected thereto.

Figure 6:
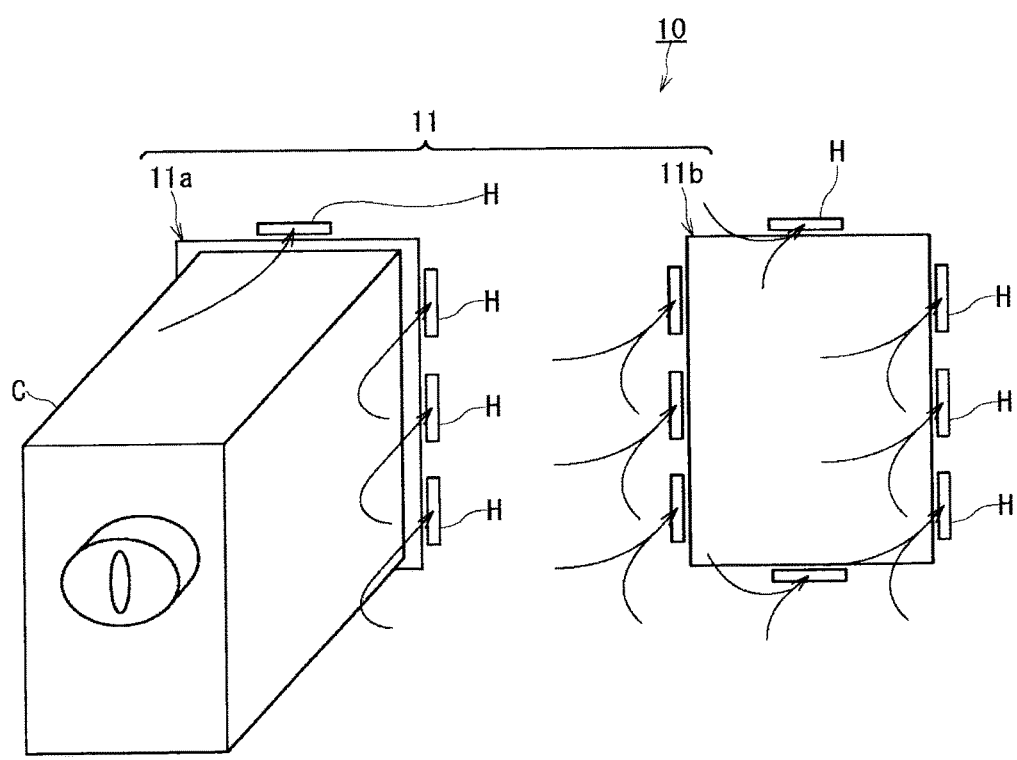
FIGS. 6 and 7 are diagrams for explaining a flow of air by the ultrasonic diagnostic apparatus relating to the first embodiment, with a probe connector being connected thereto.
Figure 7:
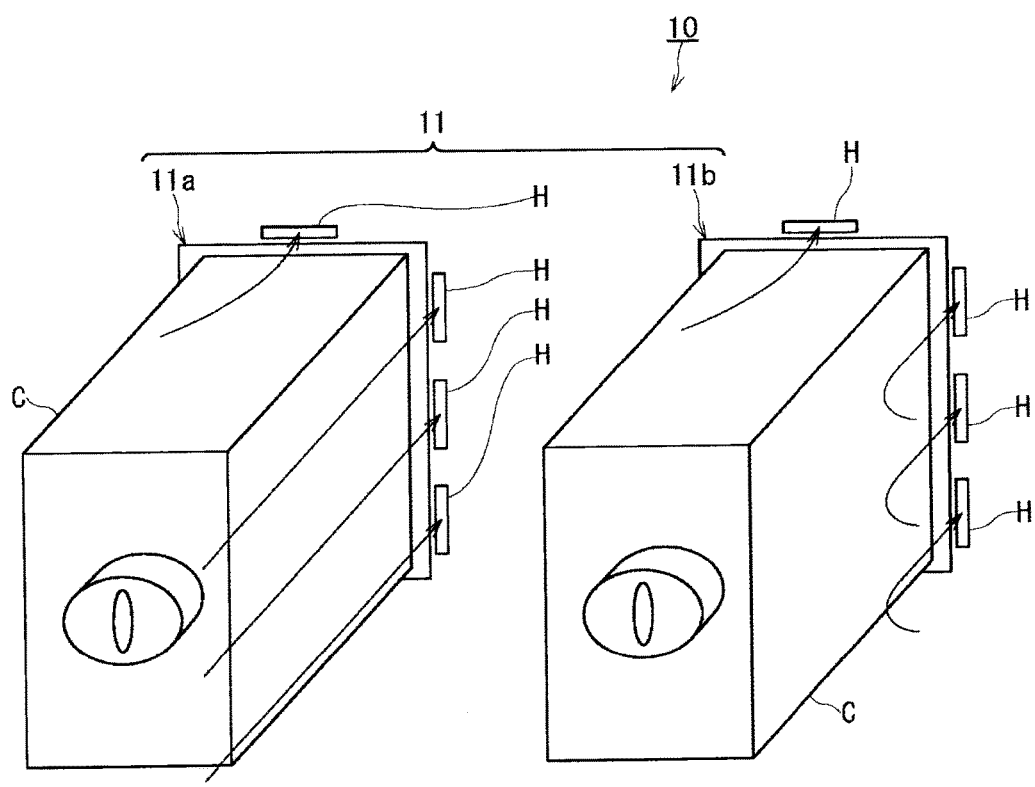

FIG. 6 illustrates a state in which one probe connector C is connected to the apparatus connector 11*a* out of the apparatus connectors 11*a* and 11*b* of the apparatus connector unit 11 illustrated in FIG. 4.

The probe connector C illustrated in FIG. 6 is connected to the apparatus connector 11*a* of the apparatus connector unit 11. The action of the blower 13 (illustrated in FIGS. 1 and 2) causes the air outside the front face of the ultrasonic diagnostic apparatus 10 to flow through an area near the surface of the probe connector C, taking heat away from the surface of the probe connector C by heat transfer, and to be drawn into vent holes H in the circumference of the apparatus connector 11*a*, respectively (as illustrated by arrows in FIG. 6). Then, the air drawn into the ultrasonic diagnostic apparatus 10 is blown out to outside the rear face from the blower 13 via the duct tube 12 (as illustrated in FIGS. 1 and 2).

On the other hand, the action of the blower 13 causes the air outside the front face of the ultrasonic diagnostic apparatus 10 (illustrated in FIGS. 1 and 2) to be drawn into vent holes H in the circumference of the apparatus connector 11*b*, respectively (as illustrated by arrows in FIG. 6). Then, the air drawn into the ultrasonic diagnostic apparatus 10 is blown out to outside the rear face from the blower 13 via the duct tube 12 (illustrated in FIGS. 1 and 2).

FIG. 7 illustrates a state in which two probe connectors C are respectively connected to the apparatus connector 11a and the apparatus connector 11b of the apparatus connector unit 11 illustrated in FIG. 4.

The probe connectors C illustrated in FIG. 7 are connected to the apparatus connectors 11a and 11b of the apparatus connector unit 11. The action of the blower 13 (illustrated in FIGS. 1 and 2) causes the air outside the front face of the ultrasonic diagnostic apparatus 10 to flow through an area near the surface of each probe connector C, taking heat away from the surface of the probe connector C by heat transfer, and to be drawn into vent holes H in the circumference of the apparatus connectors 11a and 11b, respectively (as illustrated by arrows in FIG. 7). Then, the air drawn into the ultrasonic diagnostic apparatus 10 is blown out to outside the rear face from the blower 13 (as illustrated in FIGS. 1 and 2) via the duct tube 12 (as illustrated in FIGS. 1 and 2).

Moreover, the probe connector C being connected to the apparatus connector 11b also functions as a straightening plate for straightening the air in the right-hand outside of the probe connector C being connected to the apparatus connector 11a. Therefore, cooling effect of the probe connector C being connected to the apparatus connector 11a is higher than that in the state illustrated in FIG. 6. Similarly, the probe connector C being connected to the apparatus connector 11a also functions as a straightening plate for straightening the air in the left-hand outside of the probe connector C being connected to the apparatus connector 11b. Therefore, cooling effect of the probe connector C being connected to the apparatus connector 11b is higher than that in the state illustrated in FIG. 6. Note that, to increase the cooling effect of the probe connector C being connected to the apparatus connector 11a, a member (dummy) having a similar shape to that of the probe connector C may be connected to the apparatus connector 11b when the probe connector C is not connected to the apparatus connector 11b.

Note that in FIGS. 6 and 7, although a structure in which air is drawn into from outside the front face of the ultrasonic diagnostic apparatus 10 through vent holes H and guided to outside the rear face has been described, the structure may be such that air is guided from outside the rear face to outside the front face of the ultrasonic diagnostic apparatus 10, and is blown out to outside the front face through vent holes H. Moreover, the ultrasonic diagnostic apparatus 10 may be configured such that the air drawn in from outside the front face of the ultrasonic diagnostic apparatus 10 is blown out to inside the ultrasonic diagnostic apparatus 10 by the duct tube 12 (illustrated in FIGS. 1 and 2). In such a case, the air blown out to inside the ultrasonic diagnostic apparatus 10 is to be blown out to outside the ultrasonic diagnostic apparatus 10 through a structural gap formed in the ultrasonic diagnostic apparatus 10.

Figure 8:
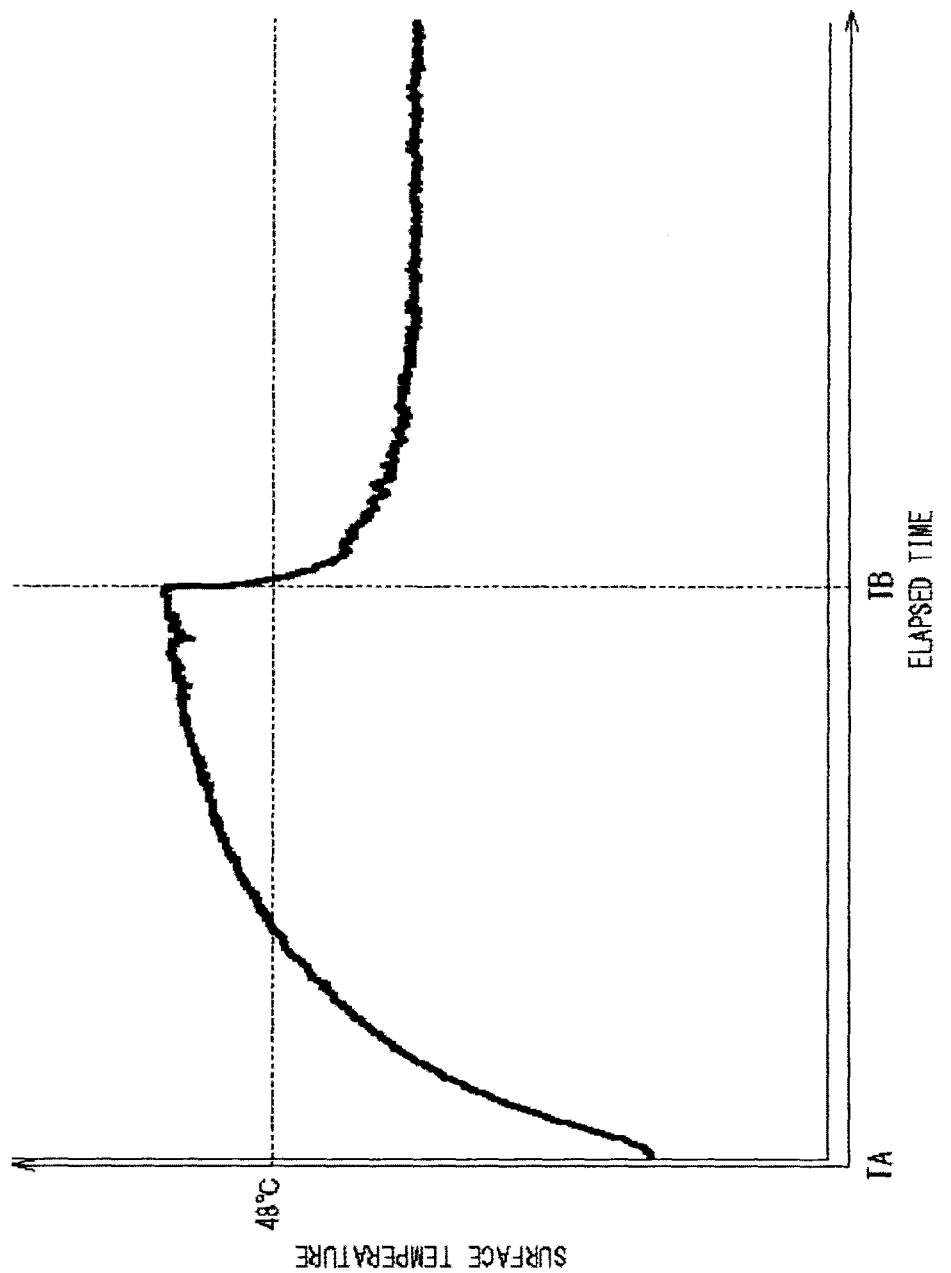
FIG. 8 is a diagram illustrating cooling effect of the probe connector in the state illustrated in FIG. 6.

FIG. 8 is a diagram illustrating cooling effect of the probe connector in the state illustrated in FIG. 6.

The abscissa illustrated in FIG. 8 shows elapsed time and the ordinate shows a surface (case) temperature (a maximum temperature among temperatures at multiple points on the surface) of the probe connector C being connected to the apparatus connector 11a. The action of the blower 13 (illustrated in FIGS. 1 and 2) was turned off at a time point TA at which scanning was started and change of the surface temperature was measured. Then, the action of the blower 13 was turned on at a time point (TB point) at which the surface temperature reached a maximum, and change of the surface temperature was measured while a gentle air flow of about 0.1 [m/s] was generated inside the duct tube 12 (illustrated in FIGS. 1 and 2) by causing air to be drawn in through the vent holes H.

According to the change of the surface temperature illustrated in FIG. 8, while the action of the blower 13 was turned off, the surface temperature of the probe connector C being connected to the apparatus connector 11a increased, significantly exceeding 48° C. However, it is seen that turning on the action of the blower 13 resulted in that the surface temperature was sufficiently cooled to below 48° C. even when there was a gentle air flow of 0.1 [m/s], thus converging to a temperature less than the aforementioned temperature. This result reveals that the ultrasonic diagnostic apparatus 10 has an excellent cooling effect of the probe connector C. Note that the surface temperature (a maximum temperature among temperatures at multiple points on the surface) of the probe connector, 48° C., is an upper limit specified by the IEC (International Electrotechnical Commission) standard.

It is generally known that due to the layout of integrated circuits installed inside the probe connector C, a side surface among surfaces of the probe connector C being connected to the apparatus connector 11a reaches a maximum temperature. The ultrasonic diagnostic apparatus 10 is particularly excellent in the cooling effect of the side surface of the probe connector C being connected to the apparatus connector 11a.

According to the ultrasonic diagnostic apparatus 10 relating to the first embodiment, since it is possible to provide a structure which can sufficiently dissipate the heat of the probe connector C even without using a special cooling structure for the probe connector C, the operator can safely use the ultrasonic probe P.

(Second Embodiment)

Using FIGS. 9 to 12, an apparatus capable of connecting a connector of ultrasonic probe relating to a second embodiment will be described. Here, description will be made taking an example in which the apparatus capable of connecting a connector of ultrasonic probe relating to the second embodiment is an ultrasonic diagnostic apparatus.

The ultrasonic diagnostic apparatus relating to the second embodiment is an apparatus according to the ultrasonic diagnostic apparatus 10 relating to the first embodiment, in which a wall part which functions as a straightening plate is provided at a location surrounding a side face of the probe connector being connected to the apparatus connector 11a (illustrated in FIGS. 1 and 2).

Figure 9:
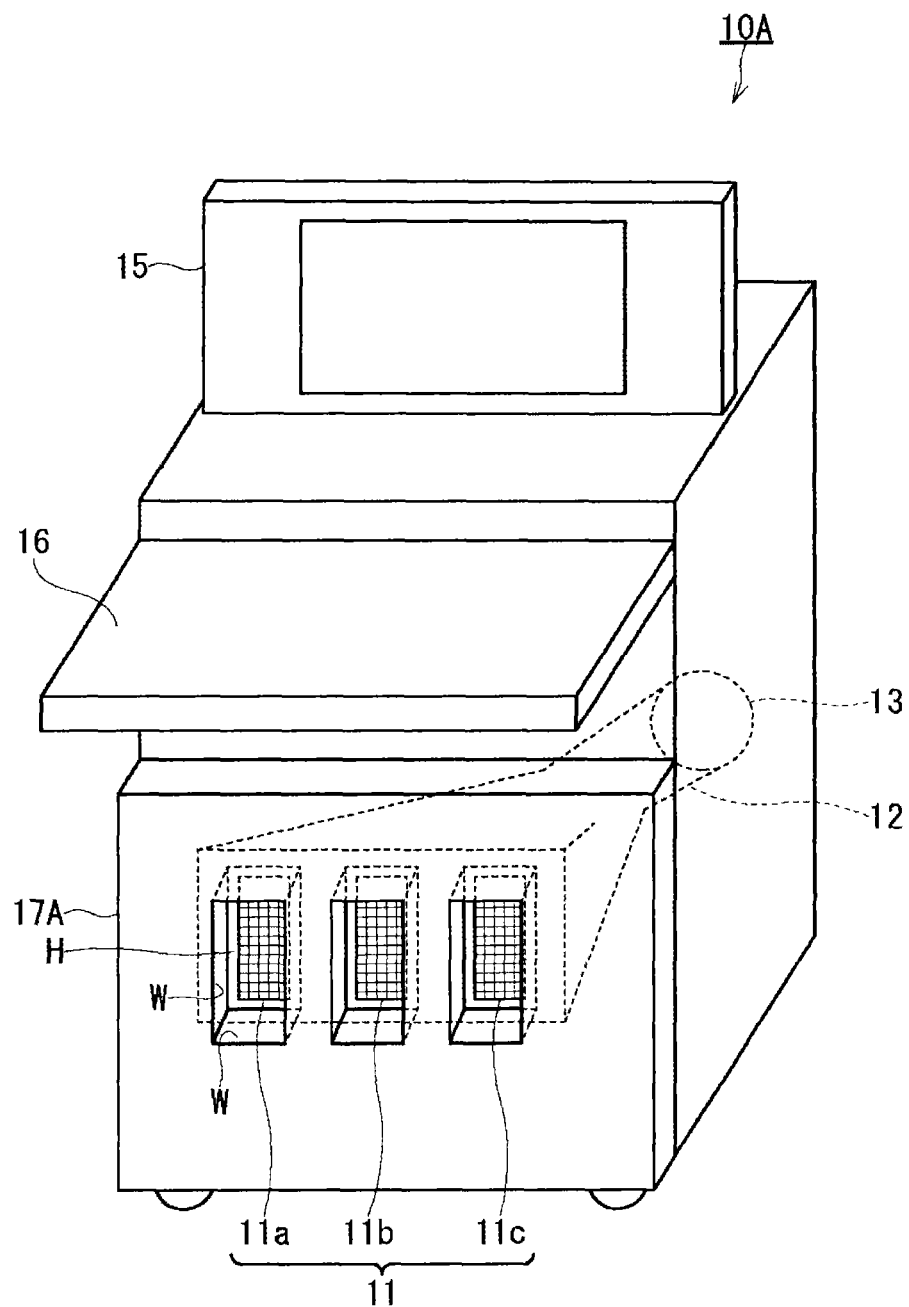
FIG. 9 is a perspective view illustrating an appearance of an ultrasonic diagnostic apparatus relating to a second embodiment.
Figure 10:
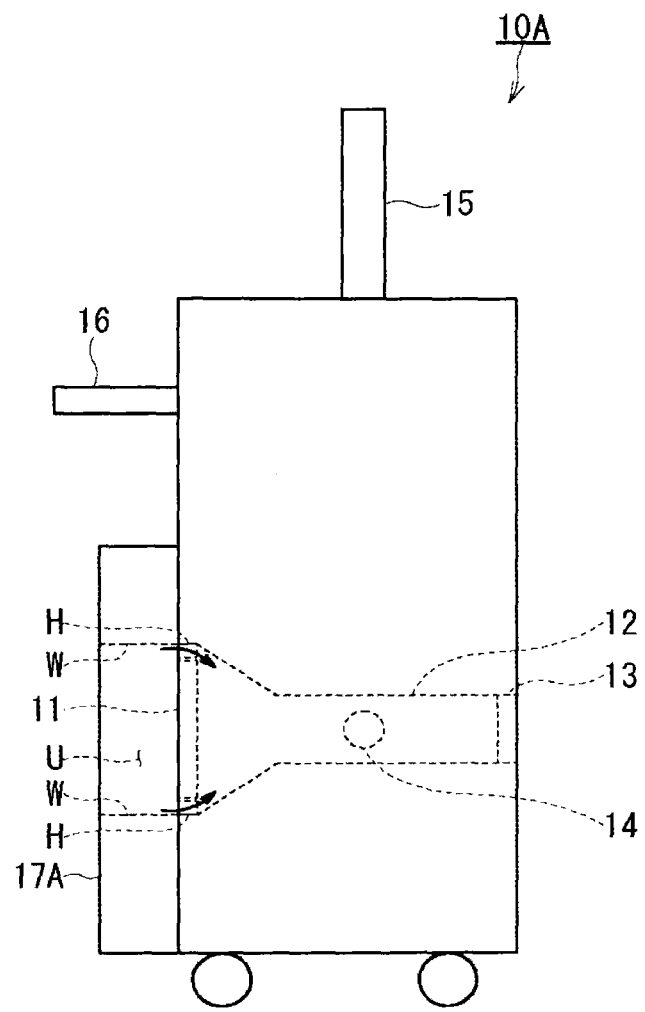
FIG. 10 is a diagram illustrating an appearance of a side face of the ultrasonic diagnostic apparatus relating to the second embodiment.

2-1. Description of Structure of Ultrasonic Diagnostic Apparatus Relating to Second Embodiment FIG. 9 is a perspective view illustrating an appearance of an ultrasonic diagnostic apparatus relating to the second embodiment. FIG. 10 is a diagram illustrating an appearance of a side face of the ultrasonic diagnostic apparatus relating to the second embodiment.

FIGS. 9 and 10 illustrate an ultrasonic diagnostic apparatus 10A relating to the second embodiment. The ultrasonic diagnostic apparatus 10A contains, in its interior, substrates with integrated circuits mounted thereon, storage devices, and so on. The ultrasonic diagnostic apparatus 10A includes an apparatus connector unit 11, a duct tube 12, a blower 13, an air velocity sensor 14, a display device 15, an input device 16, and a connector cover 17A. Note that the air velocity sensor 14 is not an indispensable component.

In the ultrasonic diagnostic apparatus 10A illustrated in FIGS. 9 and 10, like components as those of the ultrasonic diagnostic apparatus 10 illustrated in FIGS. 1 and 2 are given like reference symbols, thereby omitting detailed description thereof.

The connector cover 17A is attached so as to cover the apparatus connector unit 11. The connector cover 17A includes a wall part (side walls and upper and lower walls) W for forming a connection opening U through which the probe connector C (illustrated in FIG. 12) is respectively connectable to the apparatus connectors 11*a*, 11*b*, and 11*c*. Then, a gap having a suitable width is provided between the wall part W of the connector cover 17A forming the connection opening U and the probe connector C being connected to the apparatus connector 11*a*, 11*b*, or 11*c*. The wall part W, which forms the connection opening U, functions as a straightening plate for straightening air in an area (a gap) near the surface of the probe connector C being connected to the apparatus connector 11*a*, 11*b*, or 11*c*.

Note that FIGS. 9 and 10 illustrate a configuration in which one duct tube 12 and one blower 13 correspond to three apparatus connectors 11*a*, 11*b*, and 11*c*. However, the configuration may be such that one duct tube 12 and one blower 13 correspond to each of the three apparatus connectors 11*a*, 11*b*, and 11*c*.

Figure 11:
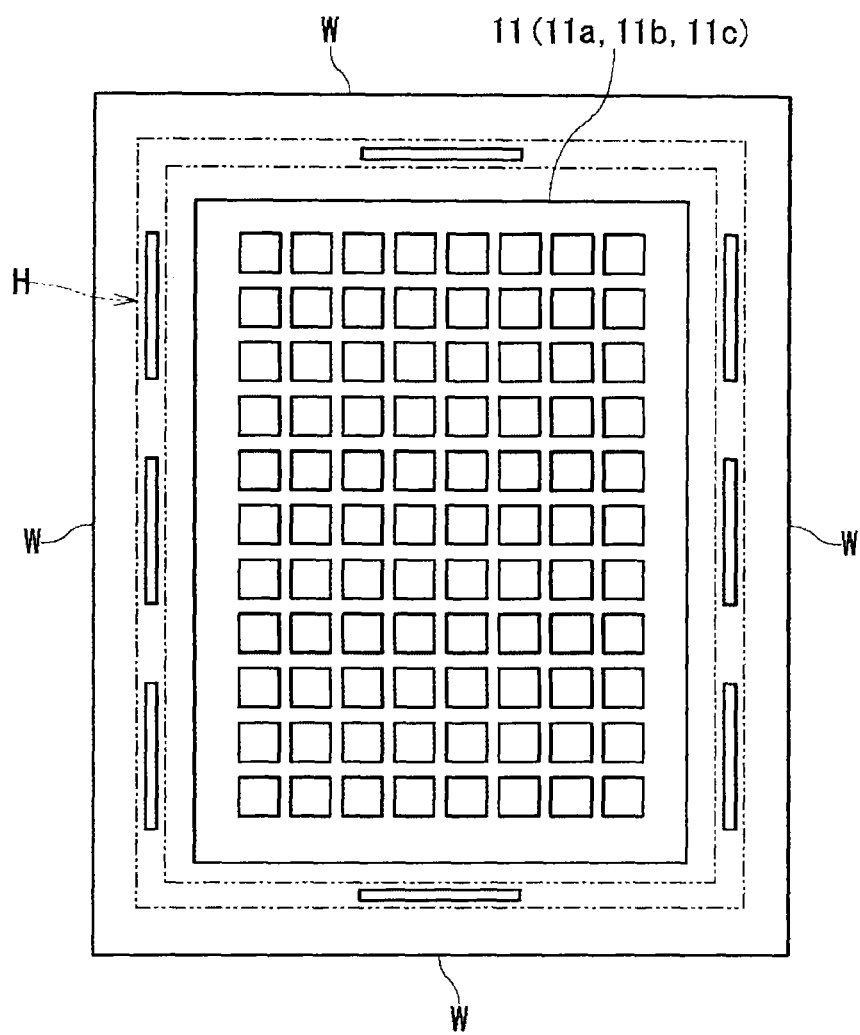
FIG. 11 is a partially enlarged view of a structural example of a wall part and an apparatus connector.

FIG. 11 is a partially enlarged view of a structural example of the wall part and the apparatus connector.

FIG. 11 illustrates an apparatus connector 11*a* (as with apparatus connectors 11*b* and 11*c*) of the apparatus connector unit 11 and a wall part W. As illustrated in FIG. 11, the apparatus connector 11*a* of the apparatus connector unit 11 is a connected part to which a connection part (pin) of the probe connector C (illustrated in FIG. 12) is connectable, and electric connection with the probe connector C can be established via the apparatus connector 11*a*. Moreover, vent holes H are formed in a circumferential portion of the apparatus connector 11*a* (as with the apparatus connectors 11*b* and 11*c*), that is, in the outside of the apparatus connector 11*a*.

The wall part W is provided at positions surrounding side faces of the probe connector C (illustrated in FIG. 12) being connected to the apparatus connector 11*a*. The vent holes H are provided between the apparatus connector 11*a* and the wall part W, and pass through from the outside to the inside of the ultrasonic diagnostic apparatus.

Returning to the description of FIGS. 9 and 10, the duct tube 12 is provided within the ultrasonic diagnostic apparatus 10A. The duct tube 12 forms a path of air between the vent holes H of the front face of the ultrasonic diagnostic apparatus 10A and the rear face of the ultrasonic diagnostic apparatus 10A.

The blower 13 is provided in the air path formed by the duct tube 12, for example, in the rear face of the ultrasonic diagnostic apparatus 10A and at an end part of the air path, and generates a flow of air in the duct tube 12. The blower 13 has a capability of drawing in the air outside the front face (in the connection opening U) of the ultrasonic diagnostic apparatus 10A to the inside thereof from the vent holes H (illustrated by arrows in FIG. 10), guiding the air drawn to the inside to the rear face of the ultrasonic diagnostic apparatus 10A via the duct tube 12, and blowing out the air guided to the rear face to outside the rear face of the ultrasonic diagnostic apparatus 10A. Alternatively, the blower 13 also has a capability of drawing in the air outside the rear face of the ultrasonic diagnostic apparatus 10A to the inside thereof, guiding the air drawn to the inside to the front face of the ultrasonic diagnostic apparatus 10A via the duct tube 12, and blowing out the air guided to the front face to outside the front face (to the connection opening U) of the ultrasonic diagnostic apparatus from the vent holes H.

2-2. Description of Internal Configuration of Ultrasonic Diagnostic Apparatus Relating to Second Embodiment Since the internal configuration of the ultrasonic diagnostic apparatus 10A relating to the second embodiment is similar to that of the ultrasonic diagnostic apparatus 10 relating to the first embodiment illustrated in FIG. 5, description thereof will be omitted.

2-3. Description of Flow of Air by Ultrasonic Diagnostic Apparatus Relating to Second Embodiment FIG. 12 is a diagram for explaining the flow of air by the ultrasonic diagnostic apparatus 10A relating to the second embodiment, with the probe connector C being connected thereto.

Figure 12:
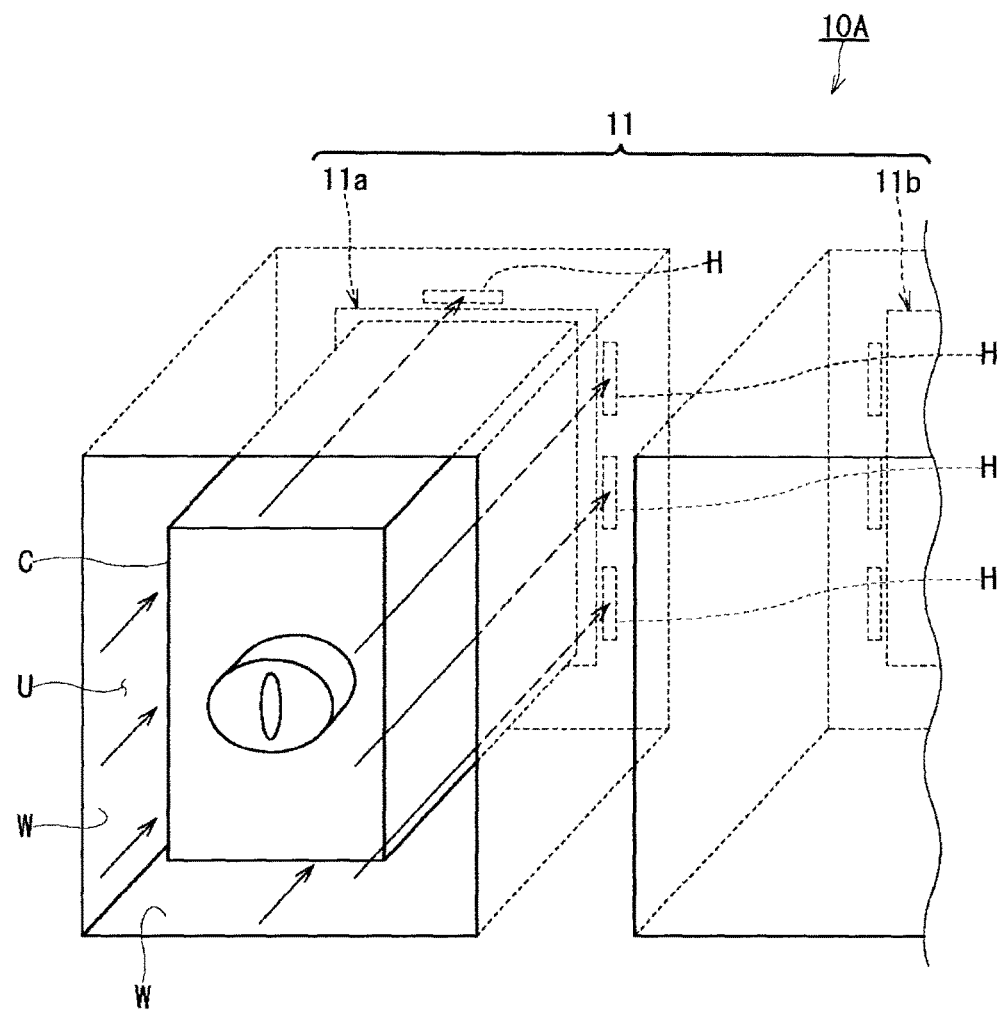
FIG. 12 is a diagram for explaining a flow of air by the ultrasonic diagnostic apparatus relating to the second embodiment, with a probe connector being connected thereto.

FIG. 12 illustrates a state in which one probe connector C is connected to the apparatus connector 11*a* out of the apparatus connectors 11*a* and 11*b* of the apparatus connector unit 11 illustrated in FIG. 4.

As illustrated in FIG. 12, the wall part W, which forms the connection opening U, functions as a straightening plate for straightening air in an area (a gap) near the surface of the probe connector C being connected to the apparatus connector 11*a*. The probe connector C illustrated in FIG. 12 is connected to the apparatus connector 11*a* of the apparatus connector unit 11 via the connection opening U. The action of the blower 13 (illustrated in FIGS. 9 and 10) causes the air outside the front face of the ultrasonic diagnostic apparatus 10A to flow along the gap between the wall part W forming the connection opening U and the probe connector C, and through an area near the surface of the probe connector C, taking heat away from the surface of the probe connector C by heat transfer, and to be drawn into vent holes H in the circumference of the apparatus connector 11*a*, respectively (as illustrated by arrows in FIG. 12). Then, the air drawn into the ultrasonic diagnostic apparatus 10A is blown out to outside the rear face.

Moreover, since the wall part W forming the connection opening U functions as a straightening plate in the flow of air in an area near the surface of the probe connector C being connected to the apparatus connector 11*a*, cooling effect of the probe connector C being connected to the apparatus connector 11*a* is higher compared to the state illustrated in FIGS. 6 and 7.

Note that in FIG. 12, although description has been made on a structure in which air is drawn in from outside the front face of the ultrasonic diagnostic apparatus 10A through the vent holes H and is guided to outside the rear face, the structure may be such that air is guided from outside the rear face of the ultrasonic diagnostic apparatus 10A to outside the front face, and is blown out to outside the front face through vent holes H. Moreover, the ultrasonic diagnostic apparatus 10A may be configured such that the duct tube 12 (illustrated in FIGS. 9 and 10) causes the air, which is drawn in from outside the front face of the ultrasonic diagnostic apparatus 10A, to be blown out to inside the ultrasonic diagnostic apparatus 10A. In such a case, the air blown out to inside the ultrasonic diagnostic apparatus 10A is blown out to outside the ultrasonic diagnostic apparatus 10A through a structural gap formed in the ultrasonic diagnostic apparatus 10A.

According to the ultrasonic diagnostic apparatus 10A relating to the second embodiment, since it is possible to provide a structure which can sufficiently dissipate the heat of the probe connector C even without using a special cooling structure for the probe connector C, the operator can safely use the ultrasonic probe P. According to the ultrasonic diagnostic apparatus 10A relating to the second embodiment, greater cooling effect of the probe connector C can be obtained compared with in the ultrasonic diagnostic apparatus relating to the first embodiment.

(Third Embodiment)

Using FIGS. 13 to 16, an apparatus capable of connecting a connector of ultrasonic probe, relating to a third embodiment, will be described. Here, description will be made taking an example in which the apparatus capable of connecting a connector of ultrasonic probe relating to the third embodiment is an ultrasonic diagnostic apparatus.

The above described ultrasonic diagnostic apparatuses 10 and 10A relating to the first and second embodiments have a structure in which vent holes H are provided between an apparatus connector and a wall part which functions as a straightening plate. On the other hand, in an ultrasonic diagnostic apparatus relating to the third embodiment, vent holes are provided in a wall part.

Figure 13:
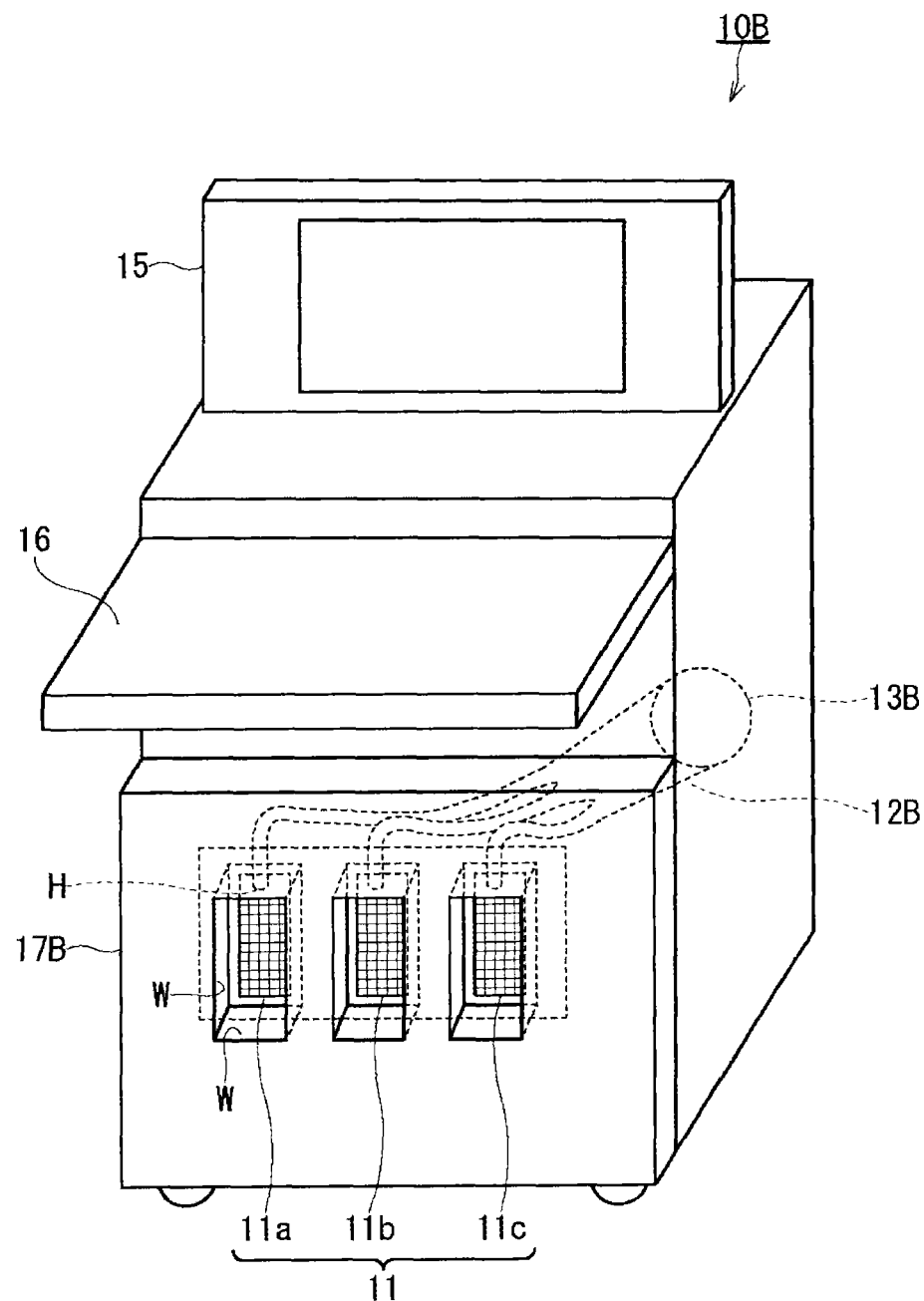
FIG. 13 is a perspective view illustrating an appearance of an ultrasonic diagnostic apparatus relating to a third embodiment.
Figure 14:
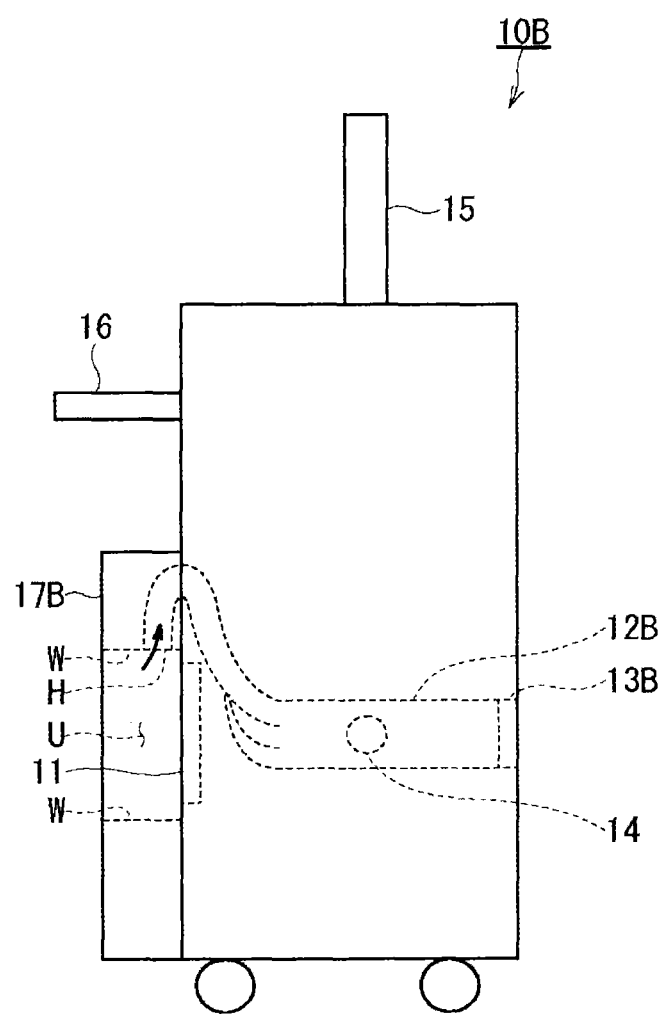
FIG. 14 is a diagram illustrating an appearance of a side face of the ultrasonic diagnostic apparatus relating to the third embodiment.

3-1. Description of Structure of Ultrasonic Diagnostic Apparatus Relating to Third Embodiment FIG. 13 is a perspective view illustrating an appearance of an ultrasonic diagnostic apparatus relating to the third embodiment. FIG. 14 is a diagram illustrating an appearance of a side face of the ultrasonic diagnostic apparatus relating to the third embodiment.

FIGS. 13 and 14 illustrate an ultrasonic diagnostic apparatus 10B relating to the third embodiment. The ultrasonic diagnostic apparatus 10B contains, in its interior, substrates with integrated circuits mounted thereon, storage devices, and so on. The ultrasonic diagnostic apparatus 10B includes an apparatus connector unit 11, a duct tube (air duct and tube, etc.) 12B, a blower (fan, etc.) 13B, an air velocity sensor 14, a display device 15, an input device 16, and a connector cover 17B. Note that the air velocity sensor 14 is not an indispensable component.

In the ultrasonic diagnostic apparatus 10B illustrated in FIGS. 13 and 14, like components as those of the ultrasonic diagnostic apparatus 10A illustrated in FIGS. 9 and 10 are given like reference symbols, thereby omitting detailed description thereof.

The apparatus connector unit 11 is provided on a side face, for example, a front face of a housing of the ultrasonic diagnostic apparatus 10B. The apparatus connector unit 11 includes three apparatus connectors 11a, 11b, and 11c to which a probe connector C (illustrated in FIG. 15) of an ultrasonic probe P (illustrated in FIG. 15) is connectable. Note that the number of the apparatus connectors may be one or more, without being limited to three. Moreover, the arrangement of the plurality of apparatus connectors will not be limited to a lateral arrangement, and may be a longitudinal, or a lateral and longitudinal arrangement.

The connector cover 17B is attached so as to cover the apparatus connector unit 11. The connector cover 17B includes a wall part (side walls and upper and lower walls) W for forming a connection opening U through which the probe connector C (illustrated in FIG. 16) is respectively connectable to the apparatus connectors 11a, 11b, and 11c. Then, a gap having a suitable width is provided between the wall part W forming the connection opening U and the probe connector C being connected to the apparatus connector 11a, 11b, or 11c. The wall part W, which forms the connection opening U, functions as a straightening plate for straightening air in an area (a gap) near the surface of the probe connector C being connected to the apparatus connector 11a, 11b, or 11c.

The duct tube 12B is provided within the ultrasonic diagnostic apparatus 10B. The duct tube 12B forms a path of air between the vent holes H of the front face of the ultrasonic diagnostic apparatus 10B and the rear face of the ultrasonic diagnostic apparatus 10B.

The blower 13B is provided in the air path formed by the duct tube 12B, for example, in the rear face of the ultrasonic diagnostic apparatus 10B and at an end part of the air path, and generates a flow of air in the duct tube 12B. The blower 13B has a capability of drawing in the air outside the front face (in the connection opening U) of the ultrasonic diagnostic apparatus 10B to the inside from the vent holes H (arrows illustrated in FIG. 14), guiding the air drawn to the inside to the rear face of the ultrasonic diagnostic apparatus 10B via the duct tube 12B, and blowing out the air guided to the rear face to outside the rear face of the ultrasonic diagnostic apparatus 10B. Alternatively, the blower 13B also has a capability of drawing in the air outside the rear face of the ultrasonic diagnostic apparatus 10B to the inside thereof, guiding the air drawn to the inside to the front face of the ultrasonic diagnostic apparatus 10B via the duct tube 12B, and blowing out the air guided to the front face to outside the front face (to the connection opening U) of the ultrasonic diagnostic apparatus 10B from the vent holes H.

Note that FIGS. 13 and 14 illustrate a configuration in which one duct tube 12B and one blower 13B correspond to three apparatus connectors 11a, 11b, and 11c. However, the configuration may be such that one duct tube 12B and one blower 13B correspond to each of the three apparatus connectors 11a, 11b, and 11c.

3-2. Description of Internal Configuration of Ultrasonic Diagnostic Apparatus Relating to Third Embodiment FIG. 15 is a schematic view illustrating an internal configuration of the ultrasonic diagnostic apparatus 10B relating to the third embodiment.

Figure 15:
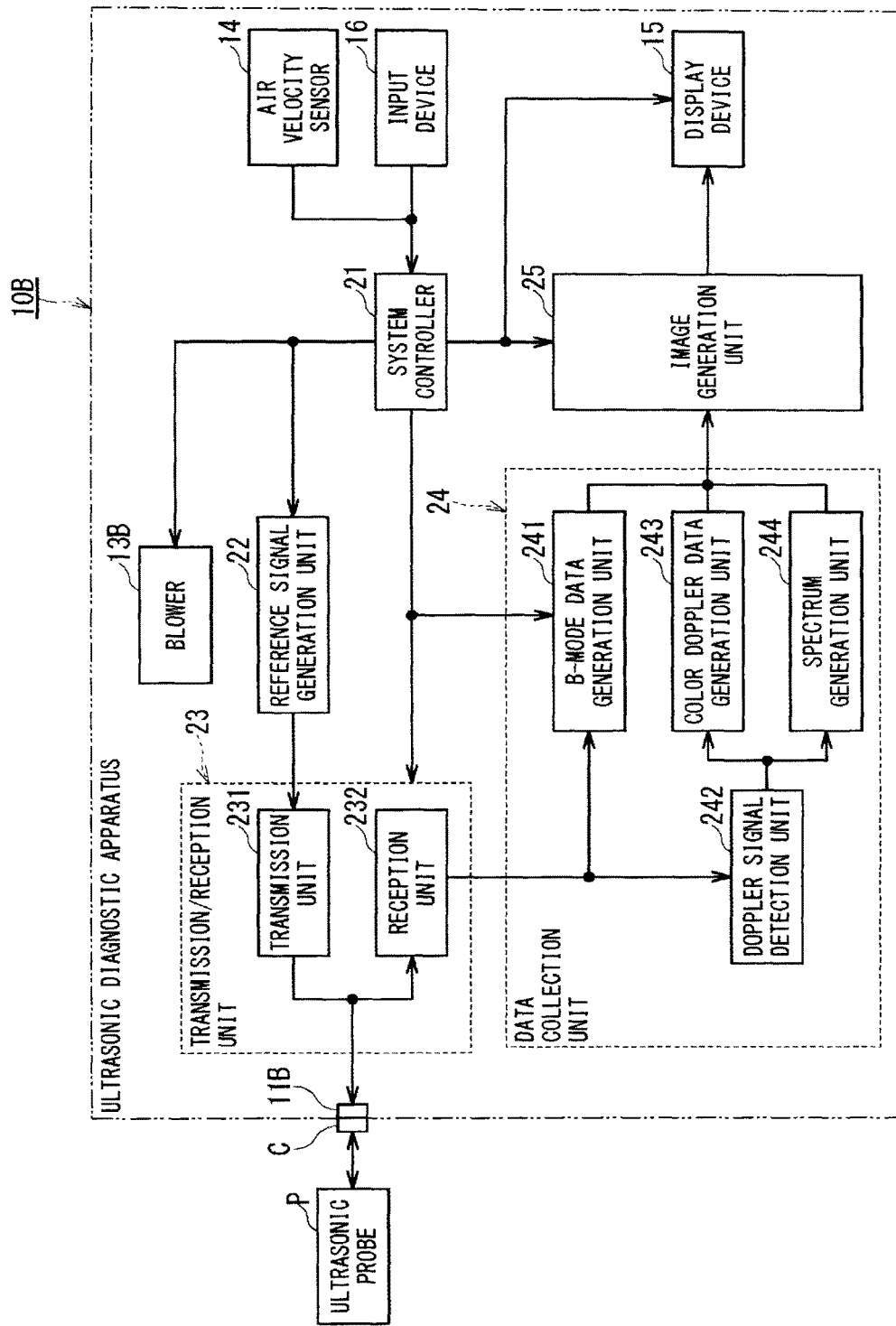
FIG. 15 is a schematic view illustrating an internal configuration of the ultrasonic diagnostic apparatus relating to the third embodiment.

FIG. 15 illustrates an ultrasonic probe P and the ultrasonic diagnostic apparatus 10B relating to the third embodiment. Note that the ultrasonic probe P and the ultrasonic diagnostic apparatus 10B combined may be referred to as an ultrasonic diagnostic apparatus.

The ultrasonic diagnostic apparatus 10B includes a blower 13B, an air velocity sensor 14, a display device 15, an input device 16, a system controller 21, a reference signal generation unit 22, a transmission/reception unit 23, a data collection unit 24, and an image generation unit 25.

In the ultrasonic diagnostic apparatus 10B illustrated in FIG. 15, like components as those of the ultrasonic diagnostic apparatus 10 illustrated in FIG. 5 are given like reference symbols, thereby omitting detailed description thereof.

Here, if the air within the duct tube 12B (illustrated in FIGS. 13 and 14) becomes not to flow due to a failure of the blower 13B or the like, the air velocity sensor 14 will detect a flow velocity not more than a threshold value. In such a case, the system controller 21 may transmit a signal to stop the action of the ultrasonic probe P.

3-3. Description of Flow of Air by Ultrasonic Diagnostic Apparatus Relating to Third Embodiment FIG. 16 is a diagram for explaining the flow of air by the ultrasonic diagnostic apparatus 10B relating to the third embodiment, with the probe connector C being connected thereto.

Figure 16:
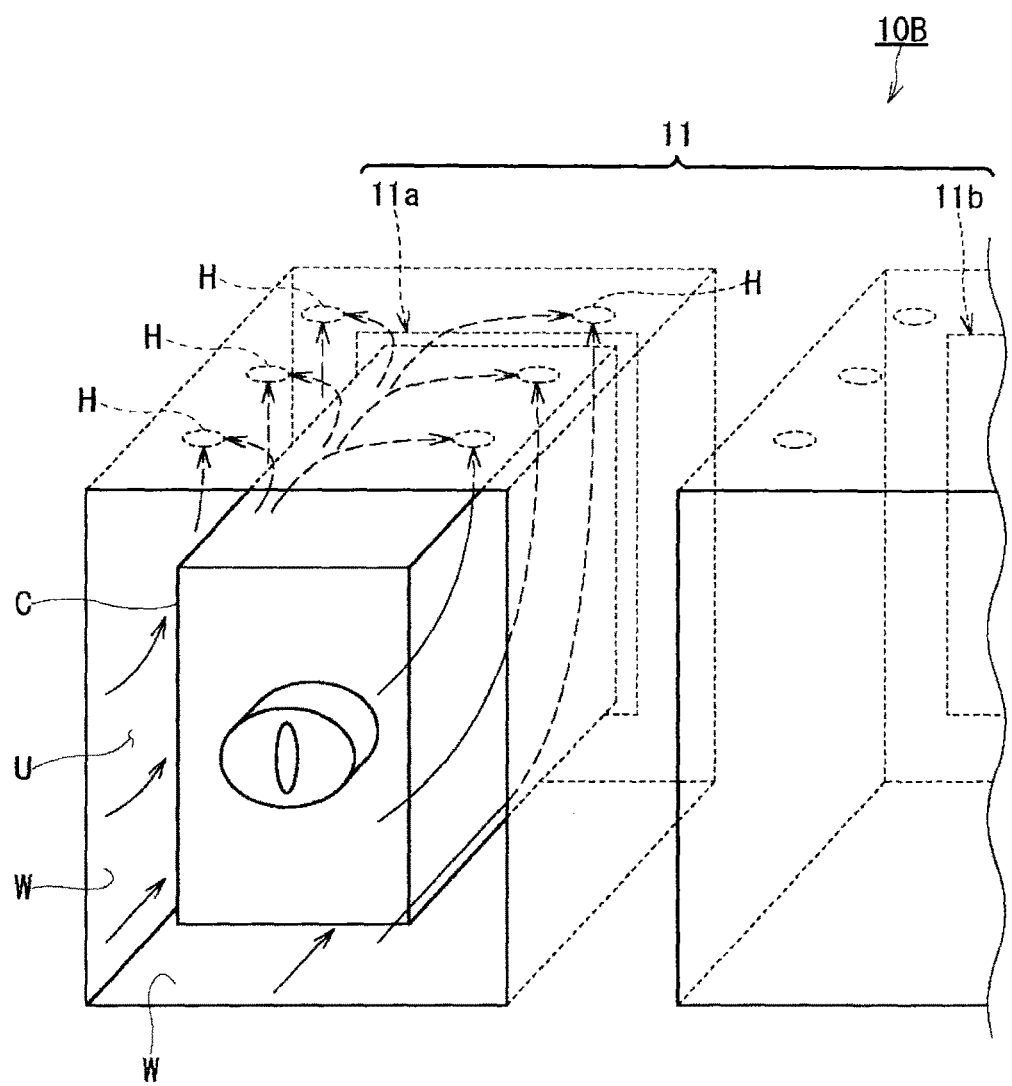
FIG. 16 is a diagram for explaining the flow of air by the ultrasonic diagnostic apparatus 10B relating to the third embodiment, with a probe connector being connected thereto.

FIG. 16 illustrates a state in which one probe connector C is connected to the apparatus connector 11a out of the apparatus connectors 11a and 11b of the apparatus connector unit 11 illustrated in FIG. 11.

As illustrated in FIG. 16, an upper wall of the wall part W forming the connection opening U has six vent holes H. Note that the number of vent holes in the upper wall forming the connection opening U may be one or more without being limited to six. Moreover, the vent hole H will have an equivalent effect even when it has a circular shape illustrated in FIG. 16, or a slit shape. Further, the location where the vent hole is provided will not be limited to the upper wall forming the connection opening U, and may be a side wall or a lower wall of the wall part W forming the connection opening U, or combination thereof.

Moreover, the vent hole H may include at least one of a dust filter for shielding dust in the air drawn to the inside through vent hole H, and an electromagnetic shield for shielding electromagnetic waves radiated by the probe connector C.

As illustrated in FIG. 16, the wall part W, which forms the connection opening U, functions as a straightening plate for straightening air in an area (a gap) near the surface of the probe connector C which is connected to the apparatus connector 11a. The probe connector C illustrated in FIG. 16 is connected to the apparatus connector 11a of the apparatus connector unit 11 via the connection opening U. The action of the blower 13B (illustrated in FIGS. 13 and 14) causes the air outside the front face of the ultrasonic diagnostic apparatus 10B to flow along the gap between the wall part W forming the connection opening U and the probe connector C and through an area near the surface of the probe connector C, taking heat away from the probe connector C by heat transfer, and to be drawn into vent holes H, respectively (as illustrated by arrows in FIG. 16). Then, the air drawn into the ultrasonic diagnostic apparatus 10B is blown out to outside the rear face.

Moreover, since the wall part W forming the connection opening U functions as a straightening plate in the flow of air in an area near the surface of the probe connector C being connected to the apparatus connector 11a, cooling effect of the probe connector C being connected to the apparatus connector 11a is higher compared to the state illustrated in FIGS. 6 and 7.

Note that in FIG. 16, although description has been made on a structure in which air is drawn in from outside the front face of the ultrasonic diagnostic apparatus 10B through the vent holes H and is guided to outside the rear face, the structure may be such that air is guided from outside the rear face of the ultrasonic diagnostic apparatus 10B to outside the front face, and is blown out to outside the front face through the vent holes H. Moreover, the ultrasonic diagnostic apparatus 10B may be configured such that the duct tube 12B (illustrated in FIGS. 13 and 14) causes the air, which is drawn in from outside the front face of the ultrasonic diagnostic apparatus 10B, to be blown out to inside the ultrasonic diagnostic apparatus 10B. In such a case, the air blown out to inside the ultrasonic diagnostic apparatus 10B is to be blown out to outside the ultrasonic diagnostic apparatus 10B through structural gaps formed in the ultrasonic diagnostic apparatus 10B.

According to the ultrasonic diagnostic apparatus 10B relating to the third embodiment, since it is possible to provide a structure which can sufficiently dissipate the heat of the probe connector C even without using a special cooling structure for the probe connector C, the operator can safely use the ultrasonic probe P. According to the ultrasonic diagnostic apparatus 10B relating to the third embodiment, greater cooling effect of the probe connector C can be obtained compared with in the ultrasonic diagnostic apparatus relating to the first embodiment.

(Fourth Embodiment)

Using FIGS. 17 to 19, an apparatus capable of connecting a connector of ultrasonic probe relating to a fourth embodiment will be described. Here, description will be made taking an example in which the apparatus capable of connecting a connector of ultrasonic probe relating to the fourth embodiment is an ultrasonic diagnostic apparatus.

The ultrasonic diagnostic apparatus relating to the fourth embodiment is a variant of the ultrasonic diagnostic apparatus 10B relating to the third embodiment.

4-1. Description of Structure of Ultrasonic Diagnostic Apparatus Relating to Fourth Embodiment FIG. 17 is a perspective view illustrating an appearance of an ultrasonic diagnostic apparatus relating to the fourth embodiment. FIG. 18 is a diagram illustrating an appearance of a side face of the ultrasonic diagnostic apparatus relating to the fourth embodiment.

Figure 17:
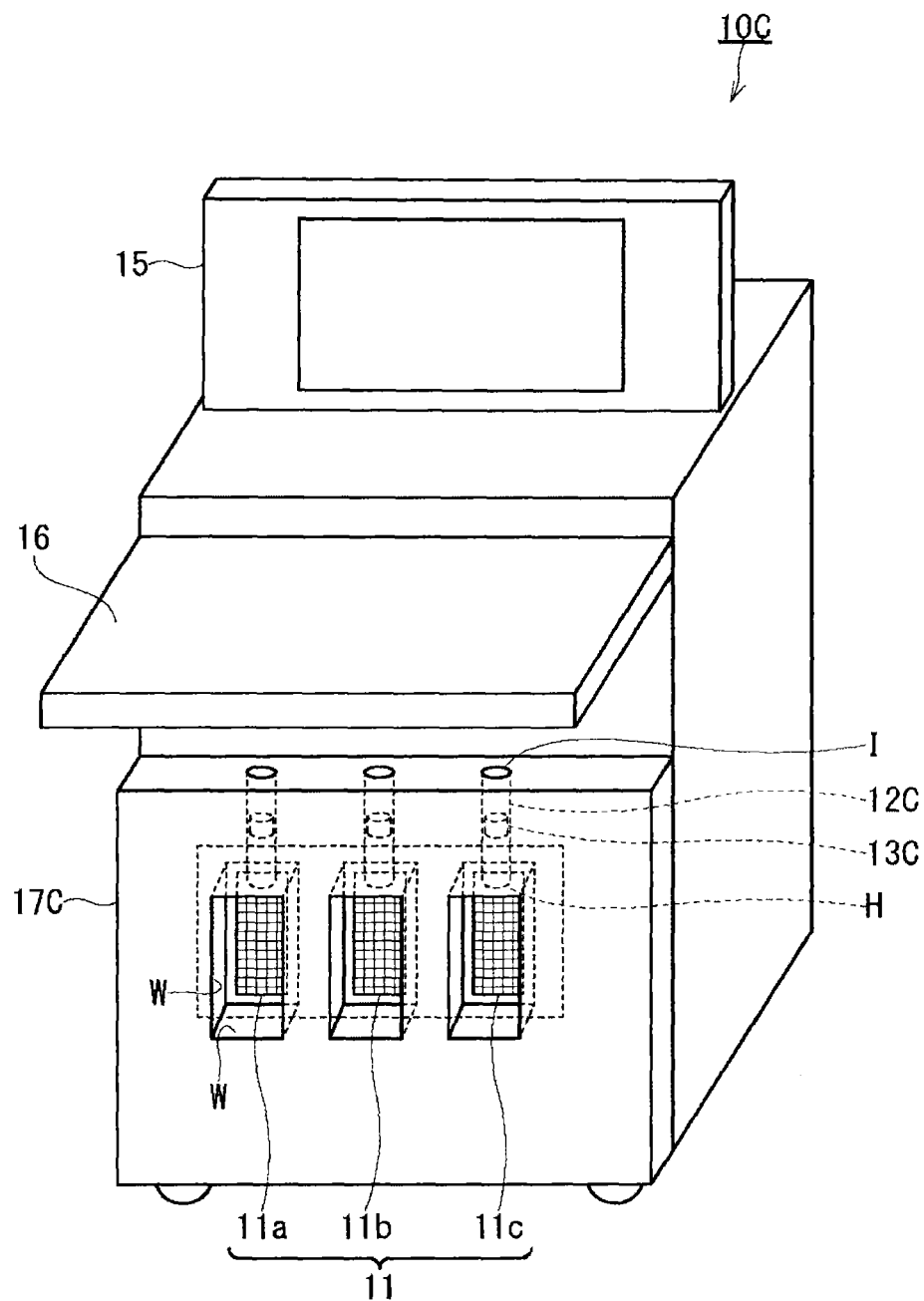
FIG. 17 is a perspective view illustrating an appearance of an ultrasonic diagnostic apparatus relating to a fourth embodiment.
Figure 18:
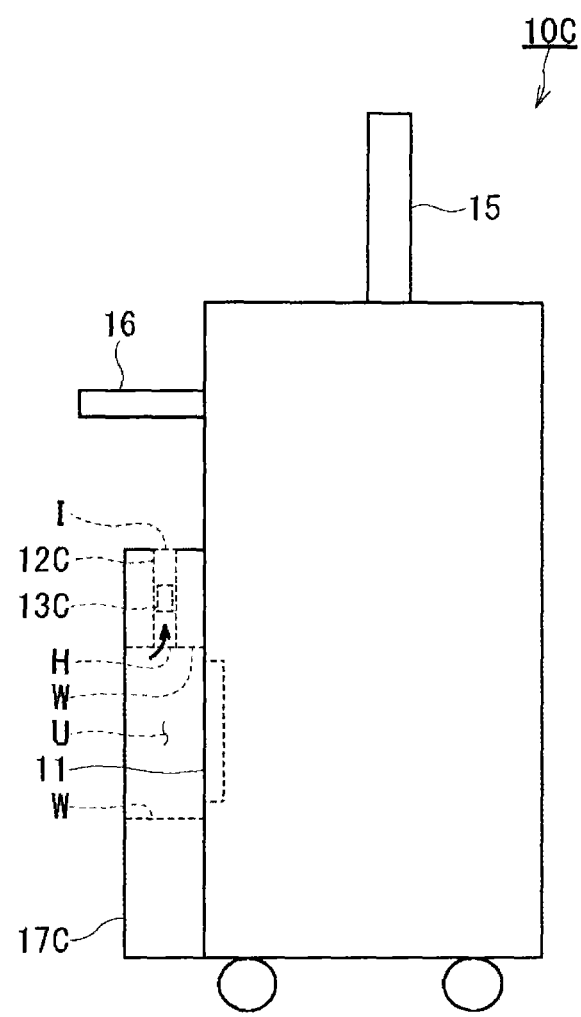
FIG. 18 is a diagram illustrating an appearance of a side face of the ultrasonic diagnostic apparatus relating to the fourth embodiment.

FIGS. 17 and 18 illustrate an ultrasonic diagnostic apparatus 10C relating to the fourth embodiment. The ultrasonic diagnostic apparatus 10C contains, in its interior, substrates with integrated circuits mounted thereon, storage devices, and so on. The ultrasonic diagnostic apparatus 10C includes an apparatus connector unit 11, a duct tube (air duct and tube, etc.) 12C, a blower (fan, etc.) 13C, an air velocity sensor 14, a display device 15, an input device 16, and a connector cover 17C. Note that the air velocity sensor 14 is not an indispensable component.

In the ultrasonic diagnostic apparatus 10C illustrated in FIGS. 17 and 18, like components as those of the ultrasonic diagnostic apparatus 10A illustrated in FIGS. 9 and 10 are given like reference symbols, thereby omitting detailed description thereof.

The connector cover 17C is attached so as to cover the apparatus connector unit 11. The connector cover 17C includes a wall part (side walls and upper and lower walls) W for forming a connection opening U through which the probe connector C (illustrated in FIG. 19) is respectively connectable to the apparatus connectors 11a, 11b, and 11c. Then, a gap having a suitable width is provided between a wall part W of the connector cover 17, which forms the connection opening U, and a probe connector C being connected to the apparatus connector 11a, 11b, or 11c. The wall part W, which forms the connection opening U, functions as a straightening plate for straightening air in an area (a gap) near the surface of the probe connector C being connected to the apparatus connector 11a, 11b, or 11c.

The connector cover 17C includes one vent hole H on an upper wall of the wall part W of the connector cover 17C, which form the connection opening U. The upper face of the connector cover 17C has one vent hole I corresponding to one vent hole H. Note that the number of the vent holes of the upper wall forming the connection opening U may be one or a plurality, without being limited to one. Moreover, the location where the vent hole is provided will not be limited to the upper wall forming the connection opening U, and may be a side wall or a lower wall of the wall part W forming the connection opening U, or combination thereof.

Moreover, the vent hole H may include at least one of a dust filter for shielding dust in the air drawn to the inside through vent hole H, and an electromagnetic shield for shielding electromagnetic waves radiated by the probe connector C.

The duct tube 12C is provided within the connector cover 17C of the ultrasonic diagnostic apparatus 10C. The duct tube 12C forms a path of air between the vent hole H provided on the wall part W forming the connection opening U and a vent hole I on the surface of the connector cover 17C.

The blower 13C is provided in the air path formed from the duct tube 12C, and generates a flow of air in the duct tube 12C. The blower 13C has a capability of drawing in the air outside the front face (in the connection opening U) of the ultrasonic diagnostic apparatus 10C to the inside thereof from the vent hole H (illustrated by arrows in FIG. 18), guiding the air drawn to the inside to the vent hole I via the duct tube 12C, and blowing out the air guided to the vent hole I to outside the front face (outside the upper face of the connector cover 17C) of the ultrasonic diagnostic apparatus 10C. Alternately, the blower 13C has a capability of drawing in the air outside the front face (outside the upper face of the connector cover 17C) of the ultrasonic diagnostic apparatus 10C to the inside thereof through the vent hole I, guiding the air drawn to the inside to the vent hole H via the duct tube 12C, and blowing out the air guided to the vent hole H to outside the front face (connection opening U) of the ultrasonic diagnostic apparatus 10C from the vent hole H.

Note that FIGS. 17 and 18 illustrate a configuration in which one duct tube 12C and one blower 13C correspond to each of three apparatus connectors 11a, 11b, and 11c. However, the configuration may be such that one duct tube 12C and one blower 13C correspond to the three apparatus connectors 11a, 11b, and 11c.

4-2. Description of Internal Configuration of Ultrasonic Diagnostic Apparatus Relating to Fourth Embodiment Since the internal configuration of the ultrasonic diagnostic apparatus 10C relating to the fourth embodiment is similar to that of the ultrasonic diagnostic apparatus 10B relating to the third embodiment illustrated in FIG. 15, description thereof will be omitted.

4-3. Description of Flow of Air by Ultrasonic Diagnostic Apparatus Relating to Fourth Embodiment FIG. 19 is a diagram for explaining the flow of air by the ultrasonic diagnostic apparatus 10C relating to the fourth embodiment, with the probe connector C being connected thereto.

Figure 19:
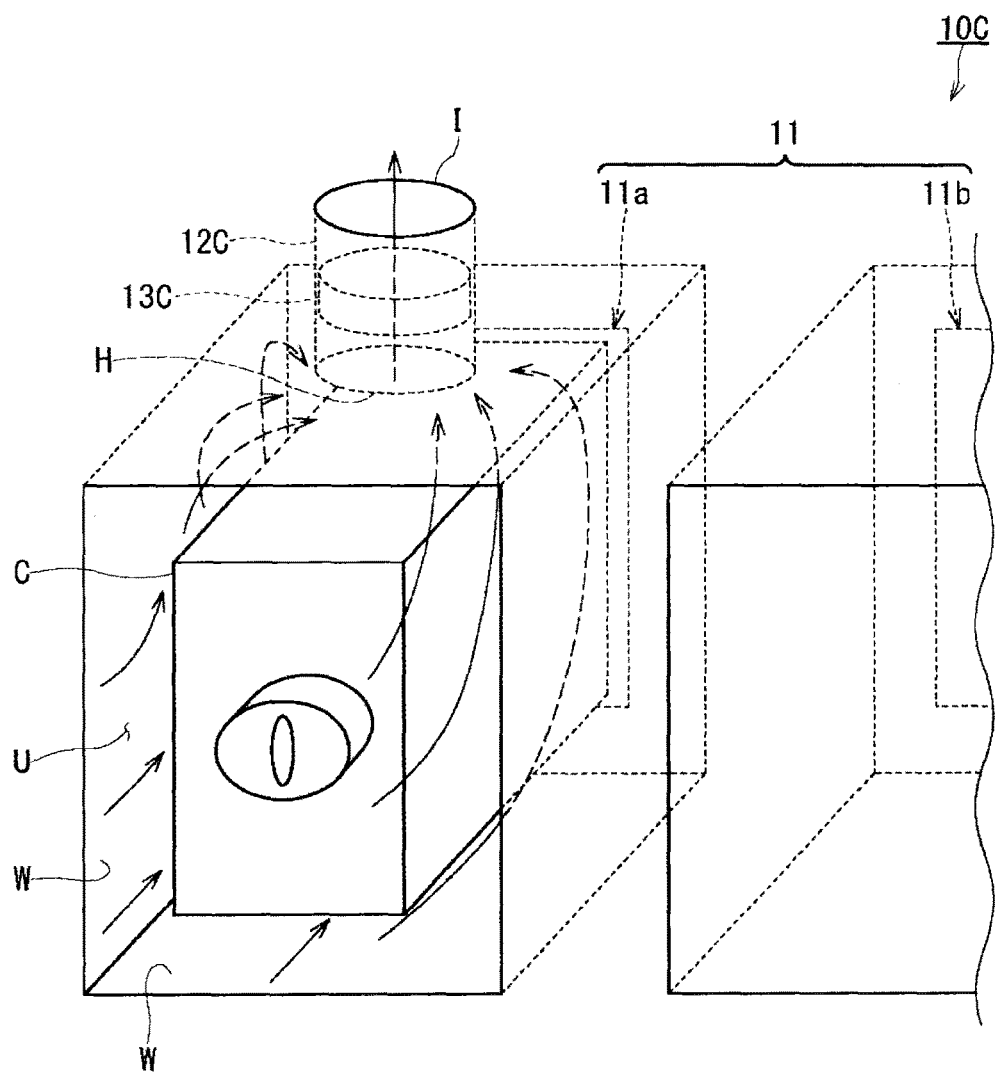
FIG. 19 is a diagram for explaining a flow of air by the ultrasonic diagnostic apparatus relating to the fourth embodiment, with a probe connector being connected thereto.

FIG. 19 illustrates a state in which one probe connector C is connected to the apparatus connector 11a out of the apparatus connectors 11a and 11b of the apparatus connector unit 11 illustrated in FIG. 11.

As illustrated in FIG. 19, an upper wall of the wall part W forming the connection opening U has one vent hole H. Note that the number of vent holes in the upper wall forming the connection opening U may be a plurality, without being limited to one. Moreover, the vent hole H will have an equivalent effect whether it has a circular shape illustrated in FIG. 19, or a slit shape. Further, the location where the vent hole is provided will not be limited to the upper wall forming the connection opening U, and may be a side wall or a lower wall of the wall part W forming the connection opening U, or combination thereof.

Moreover, the vent hole H may include at least one of a dust filter for shielding dust in the air drawn to the inside through the vent hole H, and an electromagnetic shield for shielding electromagnetic waves radiated by the probe connector C.

As illustrated in FIG. 19, the wall part W, which forms the connection opening U, functions as a straightening plate for straightening air in an area (a gap) near the surface of the probe connector C being connected to the apparatus connector 11a. The probe connector C illustrated in FIG. 19 is connected to the apparatus connector 11a of the apparatus connector unit 11 via the connection opening U. The action of the blower 13C causes the air outside the front face of the ultrasonic diagnostic apparatus 10C to flow along the gap between the wall part W forming the connection opening U and the probe connector C, and through an area near the surface of the probe connector C, taking heat away from the probe connector C by heat transfer, and to be drawn into the vent hole H in the connector cover 17C (as illustrated by arrows in FIG. 19). Then, the air drawn into the connector cover 17C is blown out to outside the front face from the vent hole I.

Moreover, since the wall part W forming the connection opening U functions as a straightening plate in the flow of air in an area near the surface of the probe connector C being connected to the apparatus connector 11a, cooling effect of the probe connector C being connected to the apparatus connector 11a is higher compared to the state illustrated in FIGS. 6 and 7.

Note that in FIG. 19, although description has been made on a structure in which air is drawn in from outside the front face of the ultrasonic diagnostic apparatus 10C through the vent hole H and is guided to a vent hole I, the structure may be such that air is guided from the vent hole I of the ultrasonic diagnostic apparatus 10C to the vent hole H, and is blown out to outside the front face through vent hole H.

According to the ultrasonic diagnostic apparatus 10C relating to the fourth embodiment, since it is possible to provide a structure which can sufficiently dissipate the heat of the probe connector C even without using a special cooling structure for the probe connector C, the operator can safely use the ultrasonic probe P. According to the ultrasonic diagnostic apparatus 10C relating to the fourth embodiment, greater cooling effect of the probe connector C can be obtained compared with in the ultrasonic diagnostic apparatus relating to the first embodiment.

(Fifth Embodiment)

Using FIGS. 20 and 21, an apparatus capable of connecting a connector of ultrasonic probe relating to a fifth embodiment will be described. Here, description will be made taking an example in which the apparatus capable of connecting a connector of ultrasonic probe relating to the fifth embodiment is a portable ultrasonic diagnostic apparatus (a laptop PC).

Figure 20:
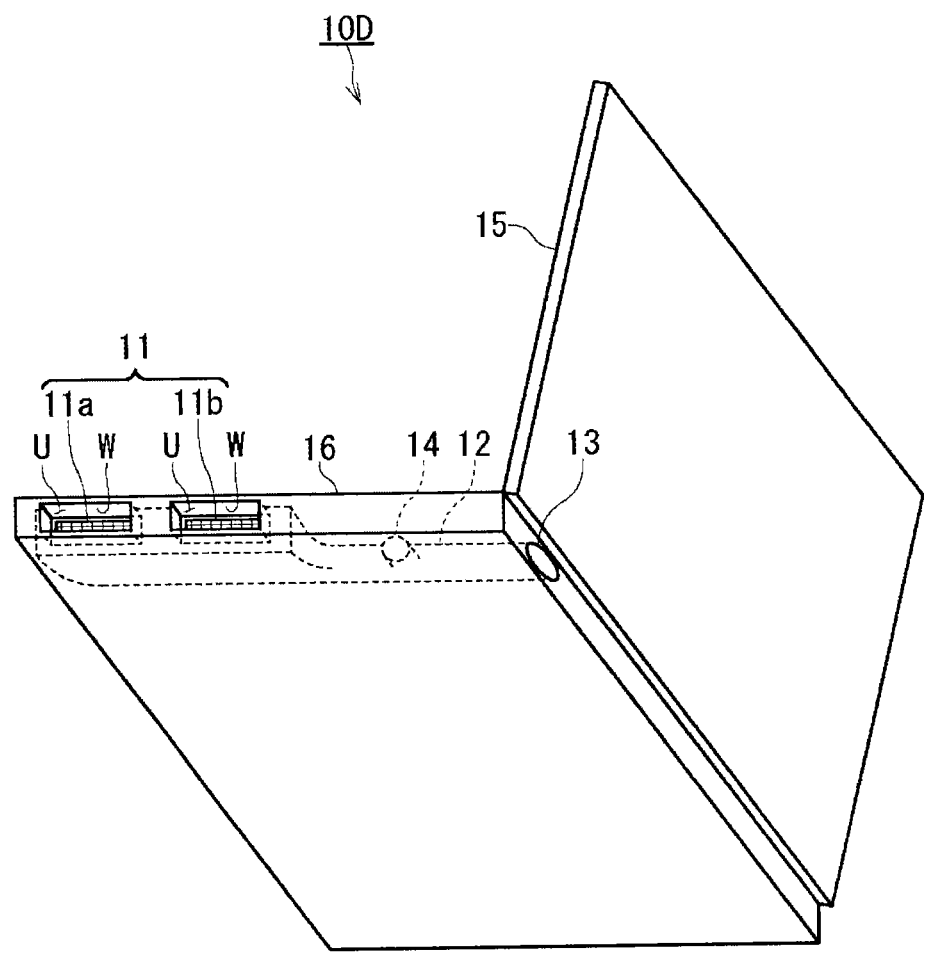
FIG. 20 is a perspective view illustrating an appearance of a portable ultrasonic diagnostic apparatus relating to a fifth embodiment.

FIG. 20 is a perspective view illustrating an appearance of a portable ultrasonic diagnostic apparatus relating to the fifth embodiment. FIG. 21 is a diagram illustrating an appearance of a side face of the portable ultrasonic diagnostic apparatus relating to the fifth embodiment.

Figure 21:
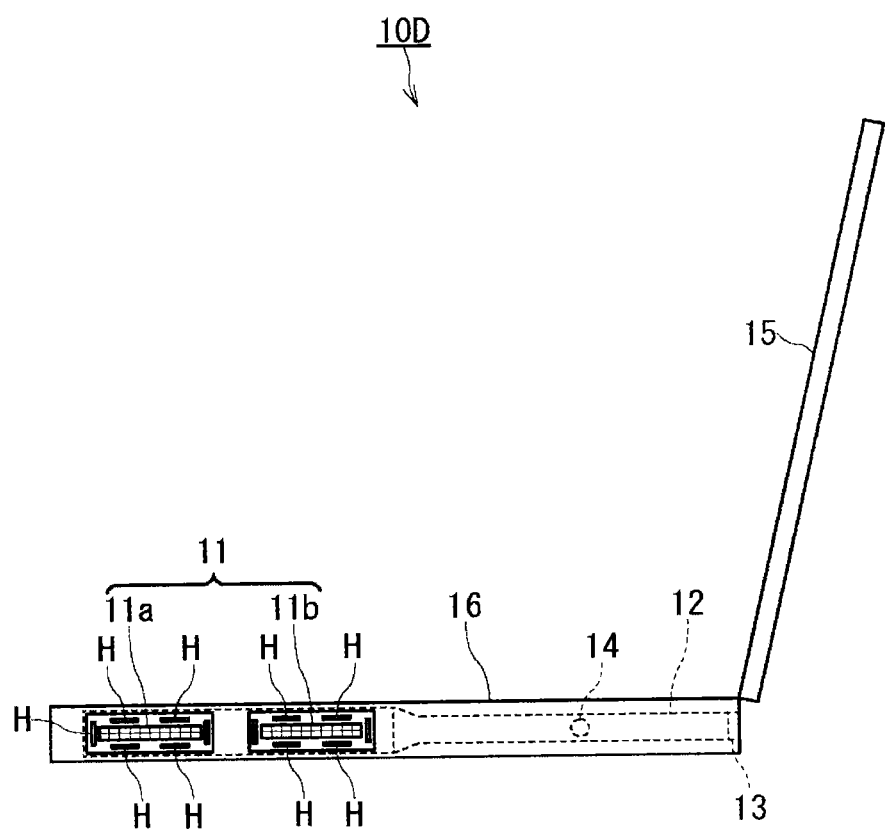
FIG. 21 is a diagram illustrating an appearance of a side face of the portable ultrasonic diagnostic apparatus relating to the fifth embodiment.

FIGS. 20 and 21 illustrate a portable ultrasonic diagnostic apparatus 10D relating to the fifth embodiment. The portable ultrasonic diagnostic apparatus 10D contains, in its interior, substrates with integrated circuits mounted thereon, storage devices, and so on. The portable ultrasonic diagnostic apparatus 10D includes an apparatus connector unit 11, a duct tube (air duct and tube, etc.) 12, a blower (fan, etc.) 13, an air velocity sensor 14, a display device 15, and an input device 16. Note that the air velocity sensor 14 is not an indispensable component.

In the portable ultrasonic diagnostic apparatus 10D illustrated in FIGS. 20 and 21, like components as those of the ultrasonic diagnostic apparatus 10A illustrated in FIGS. 9 and 10 are given like reference symbols, thereby omitting detailed description thereof.

The apparatus connector unit 11 is provided in a side face of the housing of the portable ultrasonic diagnostic apparatus 10D. The apparatus connector unit 11 includes two apparatus connectors 11a and 11b to which the probe connector C (illustrated in FIG. 15) is connectable. Note that the number of the apparatus connectors may be one or more without being limited to two.

The wall part W, which forms the connection opening U, functions as a straightening plate for straightening air in an area (a gap) near the surface of the probe connector C being connected to the apparatus connector 11a as explained by using FIGS. 11 and 12. The action of the blower 13 causes the air at the side of the portable ultrasonic diagnostic apparatus 10D to flow along the gap between the wall part W forming the connection opening U and the probe connector C, and through an area near the surface of the probe connector C, taking heat away from the probe connector C by heat transfer, and to be drawn into vent holes H in the circumference of the apparatus connector 11a, respectively. Then, the air drawn into the portable ultrasonic diagnostic apparatus 10D is blown out to outside the rear face.

Note that in FIGS. 20 and 21, although description is made on a case in which the portable ultrasonic diagnostic apparatus 10D, which is an apparatus capable of connecting a connector of ultrasonic probe, has an equivalent structure as that of the ultrasonic diagnostic apparatus 10A which forms the connection opening U as illustrated in FIGS. 9 and 10, this case is not limiting. The portable ultrasonic diagnostic apparatus 10D, which is an apparatus capable of connecting a connector of ultrasonic probe, may have an equivalent structure as that of the ultrasonic diagnostic apparatus 10B which forms the connection opening U as illustrated in FIGS. 13 and 14, or as that of the ultrasonic diagnostic apparatus 10C which forms the connection opening U as illustrated in FIGS. 17 and 18.

According to the portable ultrasonic diagnostic apparatus 10D relating to the fifth embodiment, since it is possible to provide a structure which can sufficiently dissipate the heat of the probe connector C even without using a special cooling structure for the probe connector C, the operator can safely use the ultrasonic probe P.

(Sixth Embodiment)

Using FIGS. 22 and 23, an apparatus capable of connecting a connector of ultrasonic probe relating to a sixth embodiment will be described. Here, description will be made taking an example in which the apparatus capable of connecting a connector of ultrasonic probe relating to the sixth embodiment is a transportable apparatus (docking cart) which can carry a portable ultrasonic diagnostic apparatus.

The transportable apparatus, which includes, aside from the display section of the portable ultrasonic diagnostic apparatus, a dedicated display section, an operation section, and a signal processing apparatus, receives image data acquired by the portable ultrasonic diagnostic apparatus to perform image processing thereof to make them displayed on the display section of the transportable apparatus.

Figure 22:
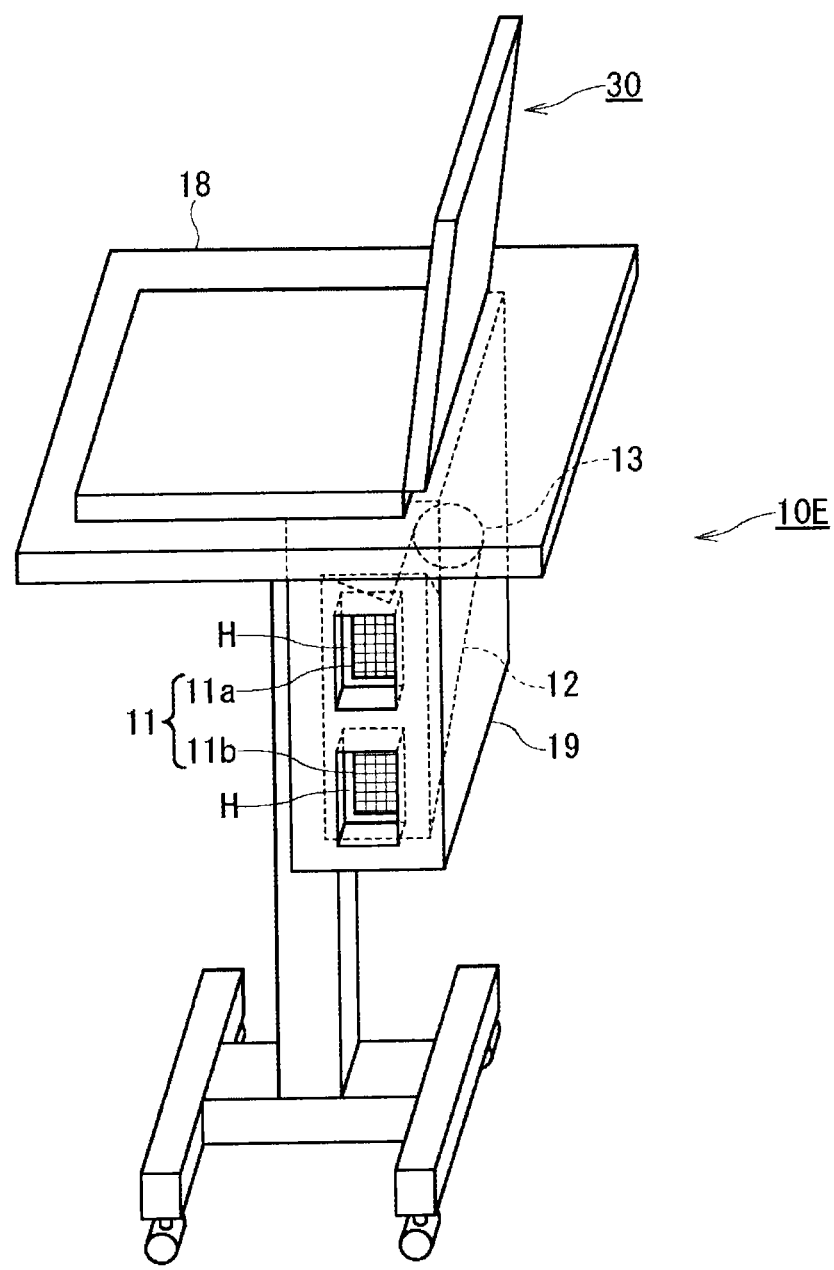
FIG. 22 is a perspective view illustrating an appearance of a transportable apparatus relating to a sixth embodiment.

FIG. 22 is a perspective view illustrating an appearance of a transportable apparatus relating to the sixth embodiment. FIG. 23 is a diagram illustrating an appearance of a side face of the transportable apparatus relating to the sixth embodiment.

Figure 23:
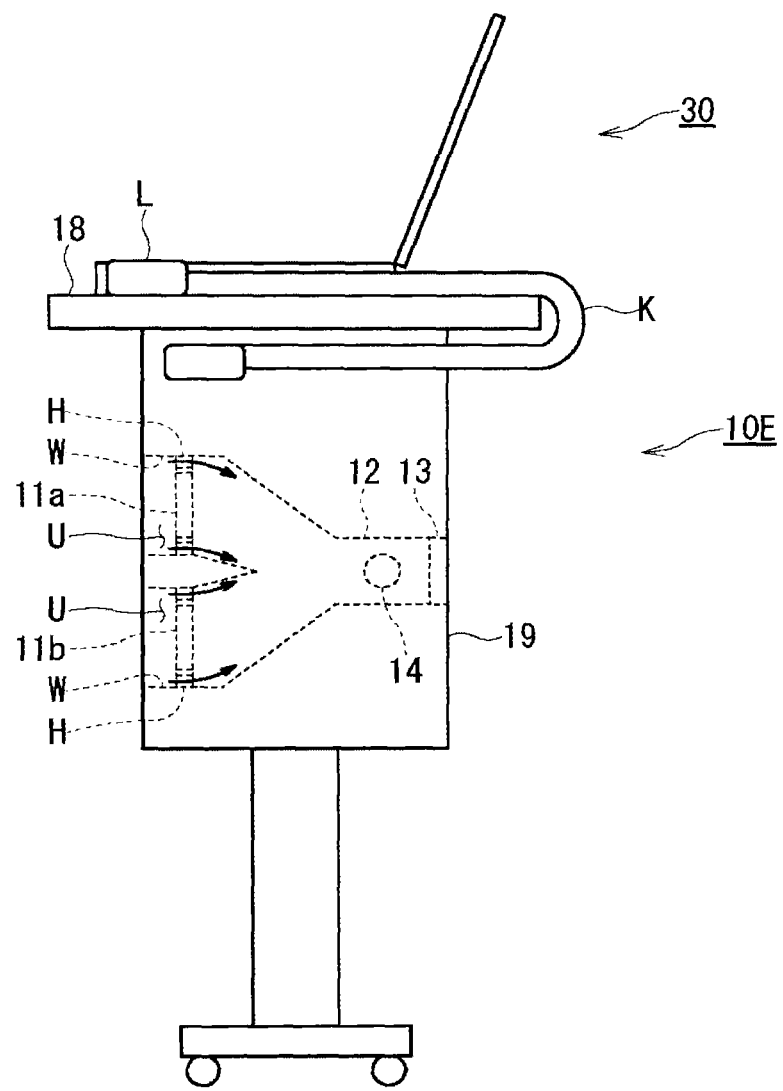
FIG. 23 is a diagram illustrating an appearance of a side face of the transportable apparatus relating to the sixth embodiment.

FIGS. 22 and 23 illustrate a portable ultrasonic diagnostic apparatus 30 and a transportable apparatus 10E according to the sixth embodiment. The transportable apparatus 10E contains, in its interior, substrates with integrated circuits mounted thereon, storage devices, and so on. The transportable apparatus 10E includes an apparatus connector unit 11, a duct tube (air duct and tube, etc.) 12, a blower (fan, etc.) 13, an air velocity sensor 14, a display device 15, and an input device 16. Note that the air velocity sensor 14 is not an indispensable component.

In the transportable apparatus 10E illustrated in FIGS. 22 and 23, like components as those of the ultrasonic diagnostic apparatus 10A illustrated in FIGS. 9 and 10 are given like reference symbols, thereby omitting detailed description thereof.

Moreover, the transportable apparatus 10E includes a top plate 18 for carrying the portable ultrasonic diagnostic apparatus 30, an extension unit 19, and a top plate support part including wheels for supporting and moving the top plate 18 and the extension unit 19.

The apparatus connector unit 11 is provided at the side of a housing of the extension unit 19. The apparatus connector unit 11 includes two apparatus connectors 11a and 11b to which the probe connector C (illustrated in FIG. 15) is connectable. Note that the number of the apparatus connector may be one or more without being limited to two.

Moreover, an extension cable K is provided with its one end being connected to the extension unit 19, and an extension connector L is provided at the other end of the extension cable K. The extension connector L is connected with a probe connection terminal of the portable ultrasonic diagnostic apparatus 30. This makes it possible to connect a plurality of probe connectors C to the portable ultrasonic diagnostic apparatus 30 via the extension unit 19.

As explained by using FIGS. 11 and 12, the wall part W, which forms the connection opening U, functions as a straightening plate for straightening air in an area (a gap) near the surface of the probe connector C being connected to the apparatus connector 11a. The action of the blower 13 causes the air at the side of the transportable apparatus 10E to flow along the gap between the wall part W forming the connection opening U and the probe connector C, and through an area near the surface of the probe connector C, taking heat away from the probe connector C by heat transfer, and to be drawn into vent holes H in the circumference of the apparatus connector 11a, respectively. Then, the air drawn into the transportable apparatus 10E is blown out to outside the rear face.

Note that in FIGS. 22 and 23, although description is made on a case in which the transportable apparatus 10E, which is an apparatus capable of connecting a connector of ultrasonic probe, has an equivalent structure as that of the ultrasonic diagnostic apparatus 10A which forms the connection opening U as illustrated in FIGS. 9 and 10, this case is not limiting. The transportable apparatus 10E, which is an apparatus capable of connecting a connector of ultrasonic probe, may have an equivalent structure as that of the ultrasonic diagnostic apparatus 10B which forms the connection opening U as illustrated in FIGS. 13 and 14, or as that of the ultrasonic diagnostic apparatus 10C which forms the connection opening U as illustrated in FIGS. 17 and 18.

According to the transportable apparatus 10E relating to the sixth embodiment, since it is possible to provide a structure which can sufficiently dissipate the heat of the probe connector C even without using a special cooling structure for the probe connector C, the operator can safely use the ultrasonic probe P.

(Variant)

By using FIG. 24, a variant of the apparatus capable of connecting a connector of ultrasonic probe, relating to the first to sixth embodiments will be described. Here, description will be made by taking for example a variant of the ultrasonic diagnostic apparatus 10A relating to the second embodiment. The variant of the ultrasonic diagnostic apparatus 10A includes an apparatus connector unit 11 which has one apparatus connector which is connectable to a probe connector.

Figure 24:
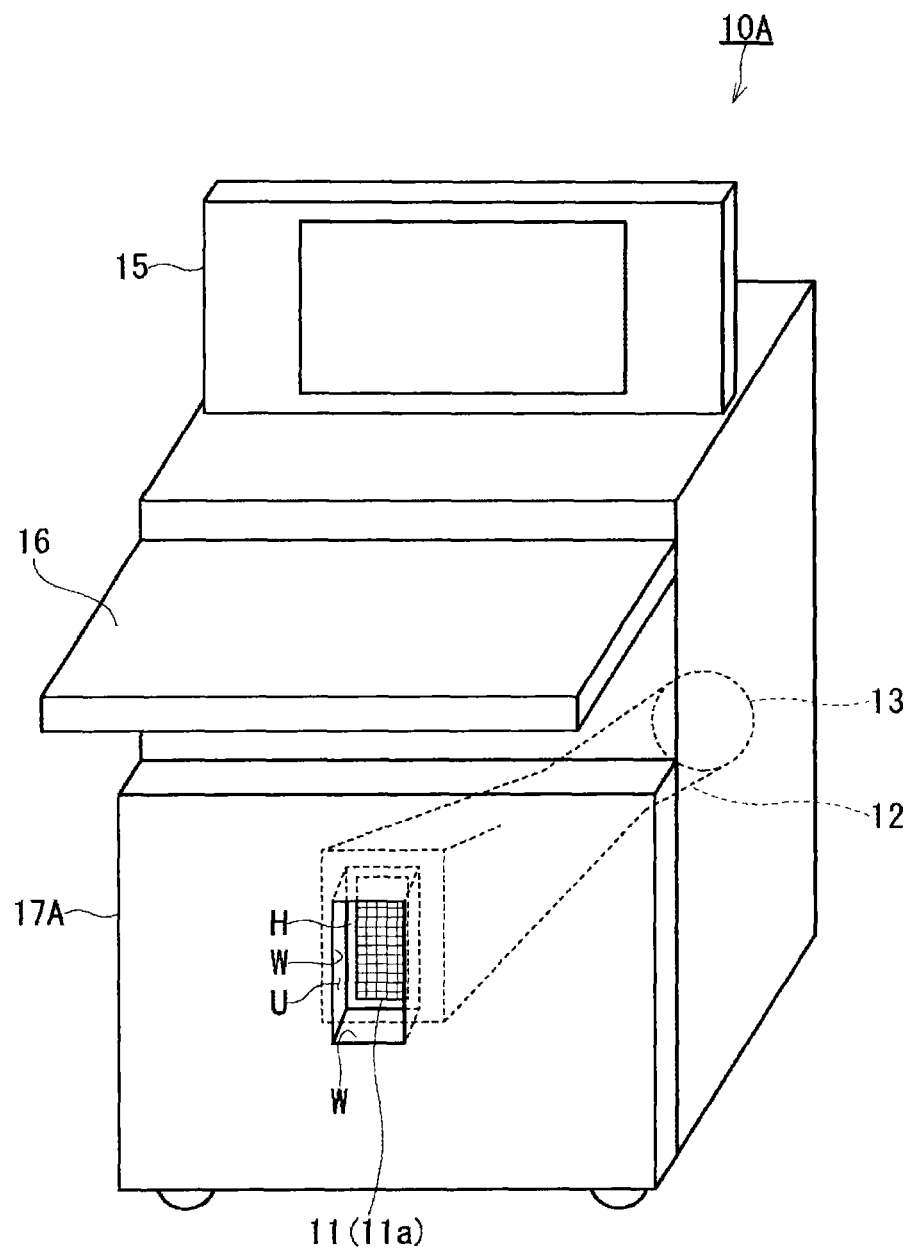
FIG. 24 is a diagram illustrating a variant of the ultrasonic diagnostic apparatus relating to the second embodiment illustrated in FIGS. 9 and 10.

FIG. 24 is a diagram illustrating a variant of the ultrasonic diagnostic apparatus relating to the second embodiment illustrated in FIGS. 9 and 10.

FIG. 24 illustrates the ultrasonic diagnostic apparatus 10A relating to the second embodiment. The connector cover 17A is attached so as to cover the apparatus connector unit 11. The connector cover 17A includes a wall part (side walls and upper and lower walls) W for forming a connection opening U through which the probe connector C (illustrated in FIG. 12) is connectable to one apparatus connector 11a. Where, a gap with a suitable width is provided between the wall part W of the connector cover 17A which forms the connection opening U and the probe connector C being connected to the apparatus connector 11a. The wall part W, which forms the connection opening U, functions as a straightening plate for straightening air in an area (a gap) near the surface of the probe connector C being connected to the apparatus connector 11a.

The duct tube 12 is provided inside the ultrasonic diagnostic apparatus 10A. The duct tube 12 forms a path of air between the vent holes H of the front face of the ultrasonic diagnostic apparatus 10A and the rear face of the ultrasonic diagnostic apparatus 10A.

The blower 13 is provided in the air path formed by the duct tube 12, for example, in the rear face of the ultrasonic diagnostic apparatus 10A and at an end part of the air path, and generates a flow of air in the duct tube 12. The blower 13 has a capability of drawing in the air outside the front face (in the connection opening U) of the ultrasonic diagnostic apparatus 10A to the inside from the vent holes H, guiding the air drawn to the inside to the rear face of the ultrasonic diagnostic apparatus 10A via the duct tube 12, and blowing out the air guided to the rear face to outside the rear face of the ultrasonic diagnostic apparatus 10A. Alternatively, the blower 13 also has a capability of drawing in the air outside the rear face of the ultrasonic diagnostic apparatus 10A, guiding the air drawn to the inside to the front face of the ultrasonic diagnostic apparatus 10A via the duct tube 12, and blowing out the air guided to the front face to outside the front face (to the connection opening U) of the ultrasonic diagnostic apparatus 10A from the vent holes H.

According to the variant of the apparatus capable of connecting a connector of ultrasonic probe, relating to the second to sixth embodiments, since it is possible to provide a structure which can sufficiently dissipate the heat of the probe connector C even without using a special cooling structure for the probe connector, the operator can safely use the ultrasonic probe P. According to the variant of the apparatus capable of connecting a connector of ultrasonic probe, relating to the second to sixth embodiments, greater cooling effect of the probe connector can be obtained compared with in the apparatus capable of connecting a connector of ultrasonic probe, relating to the first embodiment.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasound apparatus to air cool an outside of a probe connector that is connected to the ultrasound apparatus, the apparatus comprising:
 a housing having an inside and an outside;
 an electrical receptacle provided in the housing and configured to connect to a probe connector of an ultrasonic probe; and
 a vent hole provided in the housing next to the electrical receptacle and extending from the outside of the housing to the inside of the housing, the vent hole being configured such that, when the probe connector is electrically connected to the electrical receptacle, air passing through the vent hole also passes through a space between the housing and an outer-surface of the probe connector without the air passing through the probe connector.

2. The ultrasound apparatus according to claim 1, wherein
 the electrical receptacle includes a plurality of electrical receptacles;
 the housing includes a wall part provided at a location to surround side faces of the probe connector being connected to each electrical receptacle of the plurality of electrical receptacles; and
 the vent hole is provided between the each electrical receptacle and the wall part of the each electrical receptacles.

3. The ultrasound apparatus according to claim 1, wherein the ultrasound apparatus is an ultrasonic diagnostic apparatus.

4. The ultrasound apparatus according to claim 1, wherein the ultrasound apparatus is an apparatus connectable to an ultrasonic diagnostic apparatus and capable of carrying the ultrasonic diagnostic apparatus.

5. The ultrasound apparatus according to claim 1, further comprising
 a guide part configured to guide air outside the housing to inside through the vent hole.

6. The ultrasound apparatus according to claim 1, further comprising
 a guide part configured to guide air inside the housing to outside through the vent hole.

7. The ultrasound apparatus according to claim 1, wherein the vent hole includes one or more of a plurality of vent holes of a circular shape and a plurality of slits.

8. The ultrasound apparatus according to claim 1, further comprising:
 a guide part configured to guide air inside the housing;
 an air velocity sensor configured to detect a velocity of the air flowing in the guide part; and
 a control section configured to control action of the ultrasonic probe of the probe connector connected to the electrical receptacle by stopping the ultrasonic probe when the air velocity sensor detects an air velocity lower than a threshold value.

9. The ultrasound apparatus according to claim 1, wherein the vent hole includes at least one of a dust filter for filtering dust in air, and an electromagnetic shield for shielding electromagnetic waves.

10. The ultrasound apparatus according to claim 1, further comprising:
 a guide part configured to guide air inside the housing; and
 a blower configured to generate a flow of air in the guide part in such a way as to draw in air from outside to inside the housing through the vent hole or as to blow out air from inside to outside the housing through the vent hole.

11. An ultrasound apparatus to air cool an outside of a probe connector that is connected to the ultrasound apparatus, the apparatus comprising:
 a housing having an inside and an outside, and the housing including a wall part;

an electrical receptacle provided in the housing and configured to connect to a probe connector of an ultrasonic probe;

the wall part of the housing provided in a location to surround side faces of the probe connector when the probe connector is connected to the electrical receptacle; and a vent hole provided in the wall part so as to extend from the outside of the housing to the inside of the housing, the vent hole being configured such that, when the probe connector is electrically connected to the electrical receptacle, air passing through the vent hole also passes through a space between the wall part of the housing and an outer-surface of the probe connector without the air passing through the probe connector.

12. The ultrasound apparatus according to claim 11, wherein the electrical receptacle includes a plurality of electrical receptacles;

the wall part is provided at a location to surround side faces of the probe connector being connected to each electrical receptacle of the plurality of electrical receptacles; and the vent hole is provided between the each electrical receptacle and the wall part of the each electrical receptacle.

13. The ultrasound apparatus according to claim 11, wherein the apparatus is an ultrasonic diagnostic apparatus.

14. The ultrasound apparatus according to claim 11, wherein the apparatus is an apparatus connectable to an ultrasonic diagnostic apparatus and capable of carrying the ultrasonic diagnostic apparatus.

15. The ultrasound apparatus according to claim 11, further comprising a guide part configured to guide air outside the housing to inside through the vent hole.

16. The ultrasound apparatus according to claim 11, further comprising a guide part configured to guide air inside the housing to outside through the vent hole.

17. The ultrasound apparatus according to claim 11, wherein the vent hole includes one or more of a plurality of vent holes of a circular shape and a plurality of slits.

18. The ultrasound apparatus according to claim 11, further comprising:

a guide part configured to guide air inside the housing;

an air velocity sensor configured to detect a velocity of the air flowing in the guide part; and a control section configured to control action of the ultrasonic probe of the probe connector connected to the electrical receptacle by stopping the ultrasonic probe when the air velocity sensor detects an air velocity lower than a threshold value.

19. The ultrasound apparatus according to claim 11, wherein the vent hole includes at least one of a dust filter for filtering dust in air, and an electromagnetic shield for shielding electromagnetic waves.

20. The ultrasound apparatus according to claim 11, further comprising:

a guide part configured to guide air inside the housing; and a blower configured to generate a flow of air in the guide part in such a way as to draw in air from outside to inside the housing through the vent hole or as to blow out air from inside to outside the housing through the vent hole.

* * * * *